US012788268B2

(12) United States Patent
Abel et al.

(10) Patent No.: US 12,788,268 B2
(45) Date of Patent: Nov. 10, 2026

(54) MULTI-VOXEL PRESCRIPTION FOR LUMBAR DISC EVALUATION

(71) Applicant: ACLARION, INC., San Mateo, CA (US)

(72) Inventors: James Charles Abel, Emerald Hills, CA (US); Ricardo Dario Pradenas, Irvine, CA (US)

(73) Assignee: Aclarion, Inc., Broomfield, CO (US)

( * ) Notice: Subject to any disclaimer, the term of this patent is extended or adjusted under 35 U.S.C. 154(b) by 189 days.

(21) Appl. No.: 18/917,748

(22) Filed: Oct. 16, 2024

(65) Prior Publication Data

US 2026/0102075 A1 Apr. 16, 2026

(51) Int. Cl.
*G01V 3/00* (2006.01)
*A61B 5/00* (2006.01)
*A61B 5/055* (2006.01)

(52) U.S. Cl.
CPC ............ *A61B 5/055* (2013.01); *A61B 5/4566* (2013.01); *A61B 5/7485* (2013.01)

(58) Field of Classification Search
CPC ...... A61B 5/055; A61B 5/4566; A61B 5/7485
USPC .......................................................... 324/309
See application file for complete search history.

(56) References Cited

U.S. PATENT DOCUMENTS 4,959,610 A 9/1990 Suzuki
4,983,920 A 1/1991 Lampman et al.
5,068,098 A 11/1991 Schweighardt et al.
5,190,039 A 3/1993 Takeuchi
5,201,311 A 4/1993 Bottomley et al.
5,207,715 A 5/1993 Fossel
5,270,651 A 12/1993 Wehrli
5,617,861 A 4/1997 Ross et al.
5,844,097 A 12/1998 Cameron, Sr. et al.
(Continued)

FOREIGN PATENT DOCUMENTS

JP S63-204143 8/1988
JP H05-509162 12/1993
(Continued)

OTHER PUBLICATIONS

Gonal et al., Classification of brain tumors by mining MRS spectrums using LabVIEW—Metabolite Peak Height Scanning Method. Open J Med Imaging. Jan. 25, 2017;7(1): 17-27.
(Continued)

*Primary Examiner* — Walter L Lindsay, Jr.
*Assistant Examiner* — Frederick Wenderoth
(74) *Attorney, Agent, or Firm* — Knobbe, Martens, Olson & Bear, LLP

(57) ABSTRACT

Systems and methods are provided for performing a magnetic resonance spectroscopy (MRS) scan of a lumber region of interest using a multi-voxel prescription. Performing the scan may include: setting a target chemical shift value for a first voxel associated with the MRS scan of the region of interest; setting an offset chemical shift value for a second voxel associated with the MRS scan of the region of interest, wherein the second voxel is spatially offset from the first voxel proportional to a difference between the target chemical shift and the offset chemical shift; locating and sizing the first voxel within the region of interest such that the second voxel, offset from the first voxel, is also within the region of interest; and performing the MRS scan on the region of interest.

20 Claims, 5 Drawing Sheets

(56) References Cited

U.S. PATENT DOCUMENTS

| | | | |
|---|---|---|---|
| 5,903,149 | A | 5/1999 | Gonen et al. |
| 6,018,675 | A | 1/2000 | Apkarian et al. |
| 6,069,478 | A | 5/2000 | Hurd |
| 6,195,409 | B1 | 2/2001 | Chang et al. |
| 6,278,891 | B1 | 8/2001 | Reiderman et al. |
| 6,418,335 | B2 | 7/2002 | Avrin |
| 6,472,871 | B2 | 10/2002 | Ryner |
| 6,549,799 | B2 | 4/2003 | Bock et al. |
| 6,552,541 | B2 | 4/2003 | Nauerth |
| 6,617,169 | B2 | 9/2003 | Ke et al. |
| 6,639,405 | B2 | 10/2003 | Liu et al. |
| 6,674,282 | B2 | 1/2004 | Pines et al. |
| 6,683,455 | B2 | 1/2004 | Ebbels et al. |
| 6,686,348 | B2 | 2/2004 | De Nanteuil et al. |
| 6,795,567 | B1 | 9/2004 | Cham et al. |
| 6,835,572 | B1 | 12/2004 | Mountford et al. |
| 6,836,114 | B2 | 12/2004 | Reddy et al. |
| 6,943,033 | B2 | 9/2005 | Van Zijl et al. |
| 6,987,997 | B1 | 1/2006 | Hurd et al. |
| 7,027,054 | B1 | 4/2006 | Cheiky et al. |
| 7,042,214 | B2 | 5/2006 | Cunningham et al. |
| 7,050,618 | B2 | 5/2006 | Belykh et al. |
| 7,116,104 | B2 | 10/2006 | Reddy et al. |
| 7,123,009 | B1 | 10/2006 | Scott |
| 7,181,348 | B2 | 2/2007 | Wishart et al. |
| 7,184,813 | B1 | 2/2007 | Hurd et al. |
| 7,288,521 | B2 | 10/2007 | Franco |
| 7,319,784 | B2 | 1/2008 | Ryner et al. |
| 7,323,871 | B2 | 1/2008 | Foo |
| 7,352,474 | B2 | 4/2008 | Bachim et al. |
| 7,411,396 | B1 | 8/2008 | Schirmer et al. |
| 7,499,745 | B2 | 3/2009 | Littrup |
| 7,514,074 | B2 | 4/2009 | Pittenger et al. |
| 7,676,254 | B2 | 3/2010 | Siddall et al. |
| 7,705,596 | B2 | 4/2010 | Witschey et al. |
| 7,741,844 | B2 | 6/2010 | Hancu et al. |
| 7,749,275 | B2 | 7/2010 | Lambrecht et al. |
| 7,831,293 | B2 | 11/2010 | Ellis et al. |
| 7,916,909 | B2 | 3/2011 | Khazen et al. |
| 7,940,264 | B2 | 5/2011 | Jojic et al. |
| 7,983,732 | B2 | 7/2011 | Chen et al. |
| 8,018,570 | B2 | 9/2011 | Kameyama |
| 8,076,936 | B2 | 12/2011 | Borthakur et al. |
| 8,208,709 | B2 | 6/2012 | Ding et al. |
| 8,223,143 | B2 | 7/2012 | Dastmalchi et al. |
| 8,233,681 | B2 | 7/2012 | Aylward et al. |
| 8,263,043 | B2 | 9/2012 | Ahrens et al. |
| 8,344,728 | B2 | 1/2013 | Majumdar et al. |
| 8,358,818 | B2 | 1/2013 | Miga et al. |
| 8,405,836 | B2 | 3/2013 | Yablon |
| 8,478,380 | B2 | 7/2013 | Soher |
| 8,553,037 | B2 | 10/2013 | Smith et al. |
| 8,569,482 | B2 | 10/2013 | Yamakawa et al. |
| 8,569,485 | B2 | 10/2013 | Kuppusamy et al. |
| 8,605,967 | B2 | 12/2013 | Dahlqvist Leinhard et al. |
| 8,609,334 | B2 | 12/2013 | Buser et al. |
| 8,615,285 | B2 | 12/2013 | Ehman |
| 8,668,647 | B2 | 3/2014 | Eskandari |
| 8,690,057 | B2 | 4/2014 | Schoening et al. |
| 8,723,516 | B2 | 5/2014 | Wheaton et al. |
| 8,761,860 | B2 | 6/2014 | Peacock, III et al. |
| 8,798,351 | B2 | 8/2014 | Ding et al. |
| 8,825,131 | B2 | 9/2014 | Peacock, III et al. |
| 8,838,201 | B2 | 9/2014 | Mori et al. |
| 8,965,094 | B2 | 2/2015 | Peacock, III et al. |
| 9,121,889 | B2 | 9/2015 | Tuchman |
| 9,138,145 | B2 | 9/2015 | Klimenko et al. |
| 9,161,735 | B2 | 10/2015 | Bradford et al. |
| 9,280,718 | B2 | 3/2016 | Claude et al. |
| 9,345,421 | B2 | 5/2016 | Peacock, III et al. |
| 9,392,959 | B2 | 7/2016 | Peacock, III et al. |
| 9,702,900 | B2 | 7/2017 | Yacobi et al. |
| 9,724,013 | B2 | 8/2017 | Peacock, III et al. |
| 9,808,177 | B2 | 11/2017 | Claude et al. |
| 9,885,766 | B2 | 2/2018 | Avdievich et al. |
| 9,901,285 | B2 | 2/2018 | Majumdar et al. |
| 10,045,711 | B2 | 8/2018 | Peacock, III et al. |
| 10,123,759 | B2 | 11/2018 | Bradford et al. |
| 10,209,330 | B2 | 2/2019 | Bottomley et al. |
| 10,251,578 | B2 | 4/2019 | Peacock, III et al. |
| 10,285,622 | B2 | 5/2019 | Peacock, III et al. |
| 10,391,142 | B2 | 8/2019 | Buser et al. |
| 10,517,504 | B2 | 12/2019 | Claude et al. |
| 10,641,854 | B2 | 5/2020 | Oz et al. |
| 10,646,135 | B2 | 5/2020 | Peacock, III et al. |
| 10,782,373 | B2 | 9/2020 | Altbach et al. |
| 11,096,603 | B2 | 8/2021 | Majumdar et al. |
| 11,179,057 | B2 | 11/2021 | Peacock, III et al. |
| 11,564,619 | B2 | 1/2023 | Lotz et al. |
| 11,633,124 | B2 | 4/2023 | Peacock, III et al. |
| 11,844,601 | B2 | 12/2023 | Peacock, III et al. |
| 12,097,020 | B2 | 9/2024 | Peacock, III et al. |
| 12,239,455 | B2 | 3/2025 | Lotz et al. |
| 12,369,813 | B2 | 7/2025 | Peacock, III et al. |
| 12,601,803 | B2 | 4/2026 | Abel et al. |
| 2001/0003423 | A1 | 6/2001 | Wald |
| 2002/0037251 | A1 | 3/2002 | Driehuys |
| 2004/0006376 | A1 | 1/2004 | Falci |
| 2004/0092809 | A1 | 5/2004 | DeCharms |
| 2004/0214348 | A1 | 10/2004 | Nicholson et al. |
| 2005/0024051 | A1 | 2/2005 | Doddrell et al. |
| 2005/0054910 | A1 | 3/2005 | Tremblay et al. |
| 2005/0240104 | A1 | 10/2005 | Shim et al. |
| 2005/0251025 | A1 | 11/2005 | Hancu et al. |
| 2006/0074292 | A1 | 4/2006 | Thomson et al. |
| 2007/0133852 | A1 | 6/2007 | Collins et al. |
| 2007/0167729 | A1 | 7/2007 | Mistretta et al. |
| 2007/0249928 | A1 | 10/2007 | Blezek et al. |
| 2007/0253910 | A1 | 11/2007 | Ahrens et al. |
| 2008/0039710 | A1 | 2/2008 | Majumdar et al. |
| 2008/0220530 | A1 | 9/2008 | Bahn et al. |
| 2008/0226148 | A1 | 9/2008 | Gu et al. |
| 2009/0034812 | A1 | 2/2009 | Nowinski et al. |
| 2009/0076481 | A1 | 3/2009 | Stegmann et al. |
| 2009/0134869 | A1 | 5/2009 | Lee |
| 2009/0191131 | A1 | 7/2009 | Fossheim et al. |
| 2009/0232378 | A1 | 9/2009 | Nakamura |
| 2009/0261823 | A1 | 10/2009 | Yu et al. |
| 2010/0085050 | A1 | 4/2010 | Dong et al. |
| 2010/0086185 | A1 | 4/2010 | Weiss |
| 2010/0121210 | A1 | 5/2010 | Lindner et al. |
| 2010/0136588 | A1 | 6/2010 | Colgin et al. |
| 2010/0166278 | A1 | 7/2010 | Witschey |
| 2010/0244834 | A1 | 9/2010 | Mori et al. |
| 2010/0264920 | A1 | 10/2010 | Witschey et al. |
| 2010/0268225 | A1 | 10/2010 | Coe et al. |
| 2010/0303358 | A1 | 12/2010 | Acharyya |
| 2010/0329529 | A1 | 12/2010 | Feldman et al. |
| 2011/0230755 | A1 | 9/2011 | MacFarlane et al. |
| 2011/0286630 | A1 | 11/2011 | Harder |
| 2012/0155731 | A1 | 6/2012 | Weersink et al. |
| 2013/0053658 | A1 | 2/2013 | Peacock et al. |
| 2013/0144155 | A1 | 6/2013 | Majumdar et al. |
| 2014/0064586 | A1 | 3/2014 | Peacock, III et al. |
| 2014/0119631 | A1 | 5/2014 | Mostafavi |
| 2014/0156573 | A1 | 6/2014 | Szyperski et al. |
| 2014/0194364 | A1 | 7/2014 | Buser et al. |
| 2014/0213887 | A1 | 7/2014 | Reddy et al. |
| 2015/0119688 | A1 | 4/2015 | Peacock, III et al. |
| 2017/0105650 | A1 | 4/2017 | Peacock, III et al. |
| 2018/0192910 | A1 | 7/2018 | Claude et al. |
| 2018/0329009 | A1 | 11/2018 | James et al. |
| 2019/0216418 | A1 | 7/2019 | Bradford et al. |
| 2019/0287674 | A1 | 9/2019 | Nitta et al. |
| 2019/0307393 | A1 | 10/2019 | Lotz et al. |
| 2020/0100698 | A1 | 4/2020 | Peacock, III et al. |
| 2020/0178889 | A1 | 6/2020 | Mountford |
| 2020/0408863 | A1 | 12/2020 | Liang et al. |
| 2022/0091208 | A1* | 3/2022 | He ........................ G01N 24/08 |
| 2022/0117552 | A1 | 4/2022 | Kim et al. |
| 2023/0140742 | A1 | 5/2023 | Abel et al. |
| 2023/0355167 | A1 | 11/2023 | Lotz et al. |
| 2023/0414126 | A1 | 12/2023 | Peacock, III et al. |
| 2024/0324892 | A1 | 10/2024 | Peacock, III et al. |

(56) References Cited

U.S. PATENT DOCUMENTS

| | | | |
|---|---|---|---|
| 2025/0098976 | A1 | 3/2025 | Peacock, III et al. |
| 2025/0318775 | A1 | 10/2025 | Lotz et al. |
| 2026/0053386 | A1 | 2/2026 | Peacock, III et al. |

FOREIGN PATENT DOCUMENTS

| | | | |
|---|---|---|---|
| JP | H06-503418 | | 4/1994 |
| JP | 2003524490 | | 8/2003 |
| JP | 2004526130 | | 8/2004 |
| JP | 2004528559 | | 9/2004 |
| KR | 1020110100046 | A | 9/2011 |
| KR | 20200118763 | A | 10/2020 |
| KR | 1020210055897 | A | 5/2021 |
| WO | WO 2006/081471 | | 8/2006 |
| WO | WO 2007/035906 | | 3/2007 |
| WO | WO 2009/058915 | | 5/2009 |
| WO | WO 2009/148550 | | 12/2009 |
| WO | WO 2010/052629 | | 5/2010 |
| WO | WO 2010/117573 | | 10/2010 |
| WO | WO 2011/047197 | | 4/2011 |
| WO | WO 2011/060237 | | 5/2011 |
| WO | WO 2011/146798 | | 11/2011 |
| WO | WO 2012/071566 | | 5/2012 |
| WO | WO 2013/155209 | | 10/2013 |
| WO | WO 2014/159288 | | 10/2014 |
| WO | WO 2017/222945 | | 12/2017 |
| WO | WO 2020/106896 | | 5/2020 |
| WO | WO 2021/108043 | | 6/2021 |
| WO | WO 2023/076606 | | 5/2023 |

OTHER PUBLICATIONS

Lee et al., Intact metabolite spectrum mining by deep learning in proton magnetic resonance spectroscopy of the brain. Mag Reson Med. Jul. 2019;82(1):33-48.

International Search Report and Written Opinion dated Feb. 13, 2026 for PCT Application No. PCT/US2025/050956 in 8 pages.

U.S. Appl. No. 16/376,879 Including its prosecution history, filed Apr. 5, 2019, Peacock III et al.

U.S. Appl. No. 16/729,222 Including its prosecution history, filed Dec. 27, 2019, Claude et al.

U.S. Appl. No. 16/840,136 Including its prosecution history, filed Apr. 3, 2020, Bradford et al.

U.S. Appl. No. 17/566,572 Including its prosecution history, filed Dec. 30, 2021, Claude et al.

"Spectroscopy reconstruction" and "Spectroscopy processing" In: "Intera Spectroscopy—Instructions for Use", Jul. 2002 (Jul. 2002), Philips Medical Systems, Netherlands, pp. 6-1 to 7-6.

Abdulkarim et al., Magnetic Resonance Imaging of the Cervical Spine: Frequency of Degenerative Changes in the Intervertebral Disc With Relation to Age. Clin. Radiol. 2003;58: 980-984.

Albert et al., Does nuclear tissue infected with bacteria following disc herniations lead to Modic changes in the adjacent vertebrae? Eur Spine J. Apr. 2013;22(4):690-696.

Albert et al., Antibiotic treatment in patients with chronic low back pain and vertebral bone edema (Modic type 1 changes): a double-blind randomized clinical controlled trial of efficacy. Eur Spine J. Feb. 13, 2013;22(4):697-707.

Arndt et al., Oct. 2012. Bacteriology of degenerated lumbar intervertebral disks. J. Spinal Disord. Tech. 25(7):E211-6.

Bandettini et al., MultiContrast Delayed Enhancement (MCODE) improves detection of subendocardial myocardial infarction by late gadolinium enhancement cardiovascular magnetic resonance: a clinical validation study. J Cardiovasc Magn Reson., vol. 14, No. I, Nov. 30, 2012 (Nov. 30, 2012).

Bartels et al., Oxygen and lactate concentrations measured in vivo in the intervertebral discs of patients with scoliosis and back pain. Spine Jan. 1998;23 (1): 1-7.

Beall et al., [Eds.] NMR Data Handbook for Biomedical Applications. New York, Pergamon Press, 1984, 11 pages.

Bechara et al., Application of a semiautomated contour segmentation tool to identify the intervertebral nucleus pulposus in MR images. AJNR Am J Neuroradiol. Oct. 2010; 31(9):1640-4.

Ben Ayed et al., Graph cuts with invariant object-interaction priors: application to intervertebral disc segmentation. Inf Process Med Imaging. 2011;22:221-32.

Bendix et al., Sep. 15, 2012. Lumbar modic changes-a comparison between findings at low-and high-field magnetic resonance imaging. Spine (Phila. Pa. 1976). 37, 1756-1762.

Bertok L., New Prospect for the Enhancement of Natural Immunity. In Natural Immunity, First Ed. Elsevier Science; Apr. 2005; pp. 289-307.

Bhanji et al., Jul.-Aug. 2002. Transient bacteremia induced by toothbrushing a companson of the Sonicare toothbrush with a conventional toothbrush. Pediatr. Dent. 24(4):295-259.

Blumenkrantz et al., A feasibility study of in vivo T1rho imaging of the intervertebral disc. Magn Reson Imaging. Oct. 2006;(24)8: 1001-1007.

Boden et al., Abnormal magnetic-resonance scans of the lumbar spine in asymptomatic subjects. A prospective investigation. J Bone & Joint Surg. 1990;72: 403-408.

Bolan et al., Measurement and Correction of Repiration-Induced Bo Variations in Breast 1H MRS at 4 Tesla. Magn Reson Med. 2004;52:1239-1245.

Boos et al. Quantitative MR Imaging of Lumbar Intervertebral Disks and Vertebral Bodies: Influence of Diurnal Water Content Variations. Radiology. vol. 188, 1993, pp. 351-354.

Boos et al. Quantitative MR Imaging of Lumbar Intervertebral Discs and Vertebral Bodies: Methodology, Reproducibility, and Preliminary Results. Magn Reson Imaging. 1994;12(4): 577-587.

Boos et al. Quantitative Magnetic Resonance Imaging of the Lumbar Spine. Spine. 1995;20(21):2358-2366.

Boos et al., Natural History of Individuals With Asymptomatic Disc Abnormalities in Magnetic Resonance Imaging; Predictors of Low Back Pain-Related Medical Consultation and Work Incapacity. Spine. 2000;25(12): 1484-1492.

Borenstein et al., The Value of Magnetic Resonance Imaging of the Lumbar Spine to Predict Low-Back Pain in Asymptomatic Subjects: A Seven-Year Follow-up Study. J Bone & Joint Surg. 2001;83: 1306-1311.

Bottomley P.A., Spatial localization in NMR spectroscopy in vivo. Ann N Y Acad Sci 1987; 508:333-348.

Bottomley et al., A review of normal tissue hydrogen NMR relaxation times and relaxation mechanisms from 1-100 MHz: Dependence on tissue type, NMR frequency, temperature, species, excision and age. Med. Phys., vol. 11, No. 4, Jul./Aug. 1984, pp. 425-448.

Brown et al., NMR chemical shift imaging in three dimensions. Proc. Natl. Acad. Sci. USA 1982; 79:3523-3526.

Brown et al., (1997). Sensory and sympathetic innervation of the vertebral endplate in patients with degenerative disc disease. J Bone Joint Surg Br 79(1): 147-153.

Buenaventura et al., Systematic review of discography as a diagnostic test for spinal pain: an update. Pain Physician 2007;10(1): 147-164.

Burke et al., MR endplate changes are associated with increased disc inflammatory mediator production. In Ortho Proceedings. J Bone Jt. Surg Br. Feb. 1, 2003;85-B(Supp II): 164.

Burke et al., Human nucleus pulposis can respond to a pro-inflammatory stimulus. Spine. Dec. 15, 2003;28(24):2685-2693.

Burstein et al., Diffusion of Small Solutes in Cartilage as Measured by Nuclear Magnetic Resonance (NMR) Spectroscopy and Imaging. J Ortho. Res., vol. 11, 1993, pp. 465-478.

Carr et al., Effects of Diffusion on Free Precession in Nuclear Magnetic Resonance Experiments. Phys Rev. May 1, 1954;94(3): 630-638.

Carragee et al., Discographic, MRI and psychosocial determinants of low back pain disability and remission: A prospective study in subjects with benign persistent back pain. Spine J. Jan. 1, 2005;5(1): 24-35.

(56) References Cited

OTHER PUBLICATIONS

Carragee et al., 2009 ISSLS Prize Winner: Does Discography Cause Accelerated Progression of Degeneration Changes in the Lumbar Disc? A Ten-year Matched Cohort Study. Spine. Oct. 1, 2009;34(21): 2338-2345.
Carragee et al., Prospective Controlled Study of the Development of Lower Back Pain in Previously Asymptomatic Subjects Undergoing Experimental Discography. Spine. May 15, 2004;29(10): 1112-1117.
Carragee et al., A gold standard evaluation of the "discogenic pain" diagnosis and determined by provocative discography. Spine Aug. 15, 2006;31(18): 2115-2123.
Carragee et al., Discography, a review. Spine J Sep. 1, 2001;1(5): 364-372.
Carragee et al., Low-pressure positive Discography in subjects asymptomatic of significant low back pain illness. Spine 2006;31(5): 505-509.
Carrino et al., Prospective evaluation of contrast-enhanced MR imaging after uncomplicated lumbar discography. Skeletal Radiol. (2007) 36:293-299.
Chen et al., Modic Changes and Disc Degeneration Caused by Inoculation of Propionibacterium acnes inside Intervertebral Discs of Rabbits: A Pilot Study. Biomed Res Int 2016:Article ID9612437 in 7 pages.
Cheng et al., "Quantitative neuropathology by high resolution magic angle spinning proton magnetic resonance spectroscopy." PNAS Jun. 10, 1997: 94(12) 6408-6413.
Cherkin et al., Physician Variation in Diagnostic Testing for Low Back Pain. Arthritis & Rheumatism, Jan. 1994; 37(1): 15-22.
Chevrefils et al., Texture analysis for automatic segmentation of intervertebral disks of scoliotic spines from MR images. IEEE Trans Inf Technol Biomed. Jul. 2009; 13(4): 608-620.
Chiu et al., Magnetic Resonance Imaging Measurement of Relaxation and Water Diffusion in the Human Lumbar Intervertebral Disc Under Compression in Vitro. Spine. Oct. 1, 2001;26(19): E437-E444.
Chung et al. Single photon emission computed tomography (SPECT) for low back pain induced by extension with No. root sign. J Chin Med Assoc. Jul. 1, 2004;67(7): 349-354. (2004).
Cohen et al., Lumbar discography: a comprehensive review of outcome studies, diagnostic accuracy, and principles. Reg Anesth Pain Med. Mar. 1, 2005;30(2): 163-183.
Comments Regarding U.S. Appl. No. 12/579,371 (Filed Oct. 14, 2009) and PCT Patent Application No. PCT/US2010/052737 (Filed Oct. 14, 2010).
Coppes et al., Innervation of "painful" lumbar discs. Spine. Oct. 15, 1997;22(20): 2342-2349.
Cunningham et al., Design of symmetric-sweep spectral-spatial RF pulses for spectral editing. Magn Reson Med Jul. 2004;52(1): 147-153.
Dalca et al., Segmentation of nerve bundles and ganglia in spine MRI using particle filters. Med Image Comput Comput Assist Interv. 2011; 14(Pt 3): 537-545.
Derby et al., Analgesic Discography: Can Analgesic Testing Identify a Painful Disc? SpineLine Nov.-Dec. 2008;17-24.
Derincek et al., Discography: Can pain in a morphologically normal disc be due to an adjacent abnormal disc? Arch Orthop Trauma Surg. Oct. 2007; 127: 699-703.
Di Martino et al., Autoimmunity in intervertebral disc herniation: from bench to bedside. Expert Opin. Ther. Targets. Aug. 30, 2013;17(12): 1461-1470.
Diamant et al., Correlation between lactate levels and pH in discs of patients with lumbar rhizopathies. Experientia Dec. 1968;24(12): 1195-1196.
Dubey et al., Proton MR Spectroscopic Imaging of the Human Cervical Spine at 3 Tesla. Proc Int'l Soc Magn Reson Med. 13th Meeting; May 7, 2005; p. 812.
Dudli et al., Fracture of the vertebral endplates, but not equienergetic impact load, promotes disc degeneration in vitro. J Ortho Res. May 2012;30(5): 809- 816; Published online Oct. 24, 2011.
Dudli et al., Molecular and Cellular Changes in Vertebral Bone Marrow Lesions. In Annual Meeting American Academy of Orthopaedic Surgeons. Orlando; Mar. 2, 2016; Paper 454.
Dudli et al., Propionibacterium acnes infected intervertebral discs cause vertebral bone marrow lesions consistent with Modic changes. J Ortho Res. Aug. 2016. 34(8): 1447-1455.
Dudli et al., Pathobiology of Modic changes. Eur Spine J. Nov. 2016;25(11): 3723-3734.
Egger et al., Square-cut: a segmentation algorithm on the basis of a rectangle shape. PLoS One. Feb. 2012:7(2): e31064 in 13 pages.
Ellman et al., Toll-like receptor adaptor signaling molecule MyD88 on intervertebral disk homeostasis: In vitro, ex vivo studies. Gene. Jun. 10, 2012;505(2): 283-290.
Ferguson et al., Fluid flow and convective transport of solutes within the intervertebral disc. J Biomech. Feb. 1, 2004;37(2): 213-221.
Ford et al., In Vivo Quantitative Characterization of Trabecular Bone by NMR. Magn Reson Med. Feb. 1991;17(2): 543-551.
Frahm et al., Localized high-resolution proton NMR spectroscopy using stimulated echoes: Initial applications to human brain in vivo. Magn Reson Med Jan. 1989;9(1): 79-93.
Freeborn et al., Primary Care Physicians' Use of Lumbar Spine Imaging Tests: Effects of Guidelines and Practice Pattern Feedback. JGIM, Oct. 1997;12(10): 619-625.
Freemont A J., The cellular pathobiology of the degenerate intervertebral disc and discogenic back pain, (2009) Rheumatol. Jan. 1, 2009:48(1): 5-10, (Advanced access publication Oct. 14, 2008).
Freemont et al., Nerve growth factor expression and innervation of the painful intervertebral disc. J Pathol Jul. 2002; 197(3): 286-292.
Freemont et al., Nerve ingrowth into diseased intervertebral disc in chronic back pain. Lancet Jul. 19, 1997;350(9072): 178-181.
Fritzell et al., Detection of bacterial DNA in painful degenerated spinal discs in patients without signs of clinical infection. Eur Spine J. Dec. 2004;13(8): 702-706; publ. online May 8, 2004.
GÅrseth et al., Metabolic changes in the cerebrospinal fluid of patients with lumbar disc herniation or spinal stenois. J Neurosci Res. Sep. 1, 2002;69(5): 692-695.
Giulietti et al., Semiautomated segmentation of the human spine based on echoplanar images. Magn Reson Imaging. Dec. 2011; 29(10):1429-1436.
Gornet et al., Magentic Resonance Spectroscopy (MRS) can identify painful lumbar dics and mayfacilitate improved clinical outcomes of lumbar surgeries for discogenic pain. Eur Spine J. Apr. 1, 2019;28: 674-6787; published onine on Jan. 4, 2019.
Groupille et al., Matrix Metalloproteinases: The Clue to Intervertebral Disc Degeneration?—Spine. Jul. 15, 1998;23(14): 1612-1626.
Grunhagen et al., Nutrient supply and intervertebral disc metabolism. J Bone Joint Surg. Apr 1;88(Suppl 2): 30-35.
Gundry et al., Magnetic Resonance Imaging of the Musculoskeletal System, Part 8. The Spine, Section 1. Clin Ortho Related Res. May 1, 1997;338: 275-287.
Gunzburg et al., A Cadaveric Study Comparing Discography, Magnetic Resonance Imaging, Histology, and Mechanical Behavior of the Human Lumbar Disc. Spine, Apr. 1, 1992;17(4): 417-426.
Guyer et al., Lumbar discography. Spine J. May 1, 2003;3(3): 11-27.
Hao et al., Spine disc MR image analysis using improved independent component analysis based active appearance model and Markov random field. J Biomed Engineering+heng Wu Yi Xue Gong Cheng Xue Za Zhi. Feb. 2010;27(1): 6-9.
Haro et al., Matrix metalloproteinase-7-dependent release of tumor necrosis factor in a model of herniated disc resorption. J Clin Invest. Jan. 2000; 105(2): 143-150.
Hassler O., The Human Intervertebral Disc: A Micro-Angiographical Study on Its Vascular Supply at Various Ages. Acta Orthop Scandinav. Jan. 1, 1969;40(6): 765-772.
Henning et al., Spinal cord MRS in and beyond the cerival spine. Proc Inter'l Soc Magn Reson Med. May 6, 2006; p. 889.
Hesselink J.R., Fundamentals of MR Spectroscopy. University of San Diego Spinwarp NeuroWeb. Retrieved from http://spinwarp.ucsd.edu/NeuroWeb/Text/mrs-TXT.htm; Web.archive.org Sep. 2, 2006; 4 pages.

(56) References Cited

OTHER PUBLICATIONS

Holm et al., Reactive changes in the adolescent porcine spine with disc degeneration due to endplate injury. Vet Comp Ortho Traumatol. 2007. 20(1):12-7.
Horsfield et al., Rapid semi-automatic segmentation of the spinal cord from magnetic resonance images: application in multiple sclerosis. Neuroimage. Apr. 1, 2010; 50(2): 446-555.
Huang et al., Learning-based vertebra detection and iterative normalized-cut segmentation for spinal MRI. IEEE Trans Med Imaging. May 26, 2009;28(10): 1595-1605.
Iatridis et al. Alterations in the Mechanical Behavior of the Human Lumbar Nucleas Pulposus with Degeneration and Aging, J Ortho Res. Mar. 1997;15(2): 318-322.
Immke et al., Lactate enhances the acid-sensing Na+ channel on ischemia-sensing neurons. Nat Neurosci. Sep. 1, 2001; 4(9): 869-870.
Inagawa et al., Oral administration of lipopolysaccharides for the prevention of various diseases: benefit and usefulness. Antican Res. Jul. 1, 2011;31(7):2431-2436.
Ishihara et al., Effects of low oxygen concentrations and metabolic inhibitors on proteoglycan and protein synthesis rates in the intervertebral disc. J Orthop Res Nov. 1999;17(6): 829-835.
Jain et al., Modulation of Rho GTPase activity alleviates chondroitin sulfate proteoglycan-dependent inhibition of neurite extension. J Neurosci Res Jul. 15, 2004;77(2): 299-307.
Järvinen et al., Association between changes in lumbar Modic changes and low back symptoms over a two-year period. BMC Musculoskel Disord. Dec. 2015;16(1): 1-8.
Jensen et al., Vertebral endplate signal changes (Modic change): a systematic literature review of prevalence and association with non-specific low back pain. Eur Spine J. Sep. 12, 2008;17(11): 1407-1422.
Jensen et al., Type 1 Modic changes was a significant risk factor for 1-year outcome in sick-listed low back pain patients: a nested cohort study using magnetic resonance imaging of the lumbar spine. Spine J. Nov. 1, 2014;14(11): 2568-2581.
Jiru F., Introduction to Post-Processing Techniques. Eur J Radial. Aug. 1, 2008;67(2): 202-217.
Jones et al., Axonal regeneration through regions of chondroitin sulfate proteoglycan deposition after spinal cord injury: a balance of permissiveness and inhibition. J Neurosci. Oct. 15, 2003;23(28): 9276-9288.
Kadoury et al., Personalized X-ray 3-D reconstruction of the scoliotic spine from hybrid statistical and image-based models. IEEE Trans Med Imaging. Sep. 2009;28(9): 1422-1435.
Kang et al., Towards a Biochemical Understanding of Human Intervertebral Disc Degeneration and Herniation: Contributions of Nitric Oxide, Interleukins, Prostaglandin E2, and Matrix Metalloproteinases. Spine. May 15, 1997;22(10): 1065-1073.
Kapsalaki et al., The Role of Proton Magnetic Resonance Spectroscopy in the Diagnosis and Categorization of Cerebral Abscesses. Neurosurgical Focus. Jun. 1, 2008;24(6):E7; 6 pages.
Kerttula et al., Modic type I change may predict rapid progressive, deforming disc degeneration: a prospective 1-year follow-up study. Eur Spine J. Jun. 2012;21(6): 1135-1142.
Keshari et al., Identification of Chondroitin Sulfate as a Marker for Human Intervertebral disc Degeneration Using Proton High Resolution Magic Angle Spinning *HR-MAS) Spectroscopy. Poster and Abstract; The 44th ENC, Mar. 30-Apr. 4, 2003, 42 pages.
Keshari et al., Characterization of intervertebral disc degeneration by high-resolution magic angle spinning (HR-MAS) spectroscopy. Magn Reson Med. Mar. 2005; 53(3): 519-527.
Keshari et al., Correlation of HR-MAS spectroscopy derived metabolite concentrations with collagen and proteoglycan levels and Thompson grade in the degenerative disc. Spine. Dec. 1, 2005;30(23): 2683-2688.
Keshari et al., Potential metabolic markers for intervertebral disc pain. Proc Intl Soc Mag Reson Med. May 9, 2006;14: 1710. May 9, 2006.
Keshari et al., Lactic acid and proteoglycans as metabolic markers for discogenic back pain. Spine. Feb. 1, 2008;33(3): 312-317.
Klapka et al., Collagen matrix in spinal cord injury. J Neurotrauma. Apr. 1, 2006;23(3-4): 422-436.
Klawitter et al., Expression and regulation of toll-like receptors (TLRs) in human intervertebral disc cells. Eur Spine J. Sep. 23, 2014;23(9): 1878-1891.
Koh et al., Automatic segmentation of the spinal cord and the dural sac in lumbar MR images using gradient vector flow field. Conf Proc IEEE Eng Med Biol Soc. Aug. 31, 2010; pp. 317-3120.
Kupče E., Applications of Adiabatic Pulses in Biomolecular Nuclear Magnetic Resonance. Meth Enzymol. 2001;338: 82-111.
Laasonen et al., Bone disease in adolescents with acne fulminans and severe cystic acne: radiologic and scintigraphic findings. Amer J Roentgenol. May 1994;162(5): 1161-1165.
Le Maitre ete al., Catabolic cytokine expression in degenerate and herniated human intervertebral discs: 1L-1ß and TNFα expression profile. Arthr Res. Ther. Aug. 2007; 9(4):R77 in 11 pages.
Li et al., Association between Lumbar Disc degeneration and Propionibacterium Acnes Infection: Clinical Research and Preliminary Exploration of Animal Experiment. Spine. Jul. 1, 2016;41(13): E764-E769.
Lin et al., 2D CSI proton MR spectroscopy of human spinal vertebra: feasibility studies. J Magn Reson Imaging. Mar. 2000;11(3): 287-293.
Liu et al., Oriented active shape models. IEEE Trans Med Imaging. Apr. 2009; 28(4): 571-584.
Liu et al., Rigid model-based 3D segmentation of the bones of joints in MR and CT images for motion analysis. Med Phys. Aug. 2008;35(8): 3637-3649.
Liu et al., Intervertebral Disk Degeneration Related to Reduced Vertebral Marrow Perfusion at Dynamic Contrast-Enhanced MRI. Amer J Radiol. Apr. 2009;192(4): 974-979.
Lorenz et al., 3D Statistical Shape Models for Medical Image Segmentation. pp. 414-423, 2nd Inter'l Conf 3-D Imaging Modeling (3DIM '99), IEEE Oct. 8, 1999; pp. 414-423.
Lotz et al., Solving Low Back Pain: If We Can't Measure It, We Can't Improve It, presented on Nov. 10, 2015, at the International Philadelphia Spine Research Symposium.
Lusins et al., SPECT and lumbar MRI in back pain with emphasis on changes in end plates in association with disc degeneration. J. Neuroimaging. Apr. 1998;8(2): 78-82; Abstract.
Lyons et al., Biochemical Changes in Intervertebral Disc Degeneration. Biochim Biophys Acta. Jan. 1, 1981;673: 443-453.
Mackiewicz et al., Receptor activator of nuclear factor kappa B ligand in an experimental intervertebral disc degeneration. Clin Exp Rheumatol. Mar. 1, 2009;27(2): 299-306.
Magnitsky et al., Quantification of Propionic Acid in the Bovine Spinal Disk After Infection of the Tissue With Propionibacteria acnes Bacteria. Spine J. Jun. 6, 2018;43(11): E634-E638.
Majumdar S., Magnetic resonance imaging and spectroscopy of the intervertebral disc. NMR In BioMed Nov. 2006;19(7): 894-903.
Majumdar S., Spectroscopic Markers of Disc Degeneration.—downloaded from CRISP website Nov. 23, 2004, 2 pages.
Maroudas A., The Biology of the Intervertebral Disc.—In Ghosh, P. el. The Biology of the Intervertebral Disc, vol. II, Chapter 9, 1988.
McDonald et al., Use of computer tomography—single-photon emission computed tomography fusion for diagnosing painful facet arthropathy. Neurosurg Focus. Jan. 1, 2007;22(1): 1-4.
McDowell et al., An expanded multilocus sequence typing scheme for propionibacterium acnes: investigation of "pathogenic", "commensal" and antibiotic resistant strains. PLoS One. Jul. 2012;7(7): e41480 in 14 pages.
McDowell et al., A new phylogenetic group of Propionibacterium acnes. J Med Microbial. Feb. 2008;57(2): 218-224.
McDowell et al., Propionibacterium acnes types I and II represent phylogenetically distinct groups. J Clin Microbiol. 2005 25;43(1): 326-334.
Michopoulou et al., Texture-based quantification of lumbar intervertebral disc degeneration from conventional T2-weighted MRI. Acta Radiologica Feb. 2011;52(1): 91-98.

(56) References Cited

OTHER PUBLICATIONS

Michopoulou et al., Atlas-based segmentation of degenerated lumbar intervertebral discs from MR images of the spine. IEEE Trans Biomed Eng. Apr. 14, 2009;56(9): 2225-2231.
Mirantes et al., Pro-inflammatory cytokines: Emerging players regulating HSC function in normal and diseased hematopoiesis. Exp Cell Res. Dec. 10, 2014;329(2): 248-254.
Modic et al., Magnetic Resonance Imaging of Intervertebral Disk Disease. Radiol. Jul. 1984;152(1): 103-111.
Modic et al., Lumbar Herniated Disk Disease and Canal Stenosis: Prospective Evaluation by Surface Coil MR, CT, and Myelography. Am J Neuroradiol. Jul. 1, 1986;7(4): 709-717.
Modic et al., Degenerative disk disease: assessment of changes in vertebral body marrow with MR imaging. Radiol. Jan. 1988;166(1): 193-199.
Modic et al., Imaging of Degenerative Disk Disease. Radiol. Jul. 1988; 168(1): 177-186.
Molliver et al., ASIC3, an acid-sensing ion channel, is expressed in metaboreceptive sensory neurons. Mol Pain Nov. 23, 2005;1: 1744-8069 in 13 pages.
Mosher et al., Human Articular Cartilage: Influence of Aging and Early Symptomatic Degeneration on the Spatial Variation of T2-Preliminary Findings at 3 T. Radiol. Jan. 2000;214(1): 259-266.
Mow et al., [Eds.] Basic Orthopaedic Biomechanics—2nd Edition; Chapter 10—Biomechanics of the Human Spine. 1997, pp. 353-393.
Mucci et al., H and C nuclear magnetic resonance identification and characterization of components of chondroitin sulfates of various origin. Carbohyd Polym. 2000;41: 37-45.
Mühl et al., Activity and DNA contamination of commercial polymerase chain reaction reagents for the universal 16S rDNA real-time polymerase chain reaction detection of bacterial pathogens in blood. Diagn Microbial Infect Dis. Jan. 1, 2010;66(1): 41-49.
Mulconrey et al., Interobserver reliability in the interpretation of diagnostic lumbar MRI and Nuclear imaging. Spine J. Mar. 1, 2006;6(2): 177-184.
Munshi et al., Nuclear Magnetic Resonance Based Profiling of Biofluids Reveals Metabolic Dysregulation in HIV Infected Persons and Those on Anti-Retroviral Therapy., PLoS One. May 16, 2013;8(5): e64298 in 9 pages.
Myheart, The Difference Between Lactic Acid and Lactate. Overview. Retrieved from https://myheart.nett/lactic-acid-2/the-diffference-between-lactic-acid-and-lactate/; Web.archive.org—Sep. 23, 2015; 6 pages.
Nachemson A., Intradiscal measurements of pH in patients with lumbar rhizopathies. Acta Orthop Scand. Jan. 1, 1969;40(1): 23-42.
Nadkarni et al., Determination of bacterial load by real-time PCR using a broad-range (universal) probe and primers set. Microbiology. Jan. 2002; 148(1): 257-266.
Naves et al., An acid-sensing ion channel that detects ischemic pain. Braz J Med Biol Res. 2005;38(11): 1561-1569.
Neubert et al., Automated detection, 3D segmentation and analysis of high resolution spine MR images using statistical shape models. Phys Med Biol. Dec. 21, 2012; 57(24): 8357-8376.
Neubert A., Automated 3D Segmentation of Vertebral Bodies and Intervertebral Discs from MRI. In 2011 Inter'l Conf Digital Image Computing IEEE Techniques and Applications. Dec. 6, 2011; pp. 19-24.
Nieminen et al., Spatial Assessment of Articular Cartilage Proteoglycans with Gd-DTPA-Enhanced T1 Imaging. Mag Reson Med., Oct. 2002;48(4): 640-648.
Niinimäki et al., Association of lumbar artery narrowing, degenerative changes in disc and endplate and apparent diffusion in disc on postcontrast enhancement of lumbar intervertebral disc. Magn Reson Mater Phy. 22:101-109 (2009).
Oegema et al., Fibronectin and its fragments increase with degeneration in the human intervertebral disc. Spine. Nov. 1, 2000;25(21): 2742-2747.
O'Neill et al., Subgroups of positive discs on discography. Spine. Oct. 1, 2004;29(19): 2134-2139.
Pacholczyk-Sienicka et al., Characterization of metabolites determined by means of 1H HR MAS NMR in intervertebral disc degeneration. MAGMA. Apr. 2015;28(2): 173-183.
Patel et al., Diffusion-weighted MRI "claw sign" improves differentiation of infectious from degenerative modic type 1 signal changes of the spine. Am J Neuroradiol. Aug. 1, 2014;35(8):1647-1652.
Pauly et al., Parameter relations for the Shinnar-Le Roux selective excitation pulse design algorithm [NMR imaging]. IEEE Trans Med Imaging Mar. 1991; 10(1): 53-65.
Pearce et al., Degeneration and the Chemical Composition of the Human Lumbar Intervertebral Disc. J Ortho Res. 1987;5(2): 198-205.
Peng Z., Automated Vertebra Detection and Segmentation from the Whole Spine MR Images. Proc 2005 IEEE Engineering Med Biol. 27th Annual Conference, Shanghai, China, Sep. 1-4, Jan. 17, 2005;pp. 2527-2530.
Perilli et al., Modic (endplate) changes in the lumbar spine: bone micro-architecture and remodelling. Eur Spine J. Sep. 2015;24(9): 1926-1934.
Petrantonaki et al., MRI Techniques for the Examination of Trabecular Bone Structure. Curr Med Imaging Rev. Jan. 1, 2005;1(1): 35-41.
Pfirrmann et al., Magnetic Resonance Classification of Lumbar Intervertebral Disc Degeneration. Spine. 2001;26(17): 1873-1878.
Piccinini et al., DAMPening inflammation by modulating TLR signalling. Mediators Inflamm. Oct. 2010;Article ID672395 in 21 pages.
Properzi et al., Chondroitin sulphate proteoglycans in the central nervous system: changes and synthesis after injury. Biochem Soc Trans. Apr. 1, 2003;31(2): 335-336.
Quero et al., Hyaluronic acid fragments enhance the inflammatory and catabolic response in human intervertebral disc cells through modulation of toll-like receptor 2 signaling pathways. Arth Res Ther. Aug. 22, 2013;15(4): R94 in 13 pages.
Rajasekaran et al., ISSLS Prize Winner: A Study of Diffusion in Human Lumbar Discs: A Serial Magnetic Resonance Imaging Study Documenting the Influence of the Endplate on Diffusion in Normal and Degenerate Discs. Spine. Dec. 1, 2004;29(23): 2654-2667.
Roberts et al., Histology and pathology of the human intervertebral disc. J Bone Joint Surg Am. Apr. 1, 2006;88(Suppl 2): 10-14.
Rollason et al., Genotypic and Antimicrobial Characterisation of Propionibacterium Acnes Isolatesfrom Surgically Excised Lumbar Disc Herniations. BioMed Res Int. Jan. 1, 2013; Article ID530382 in 7 pages.
Roughley et al., The role of proteoglycans in aging, degeneration and repair of the intervertebral disc. Biochem Soc Trans. Nov. 1, 2002;30(6): 869-874.
Rukwied et al., Potentiation of nociceptive responses to low pH injections in humans by prostaglandin E2. J Pain. May 1, 2007;8(5): 443-451.
Savvopoulou et al., Degenerative Endplate Changes of the Lumbosacral Spine: Dynamic Contrast-Enhanced MRI Profiles Related to Age, Sex, and Spinal Level. J Magn Reson Imaging Feb. 2011;33(2): 382-389.
Schiller et al., Evaluation of Cartilage Composition and Degradation by High-Resolution Magic-Angle Spinning Nuclear Magnetic Resonance. Meth Mol Med. 2004; 101:267-285.
Schiller et al., H1 and 13C HR-MAS NMR Investigations on Native and Enzymatically Digested Bovine Nasal Certilage. Magn Reson Mater Phys Biol Med. Aug. 2001;13: 19-27.
Schistad et al., The association between Modic changes and pain during 1-year follow-up in patients with lumbar radicular pain. Skeletal Radiol. Sep. 2014;43(9): 1271-1279.
Scuderi et al., A critical evaluation of discography in patients with lumbar intervertebral disc disease. Spine J Jul. 1, 2008;8(4): 624-629.
Sether et al., Intervertebral Disk: Normal Age-related Changes in MR Signal Intensity. Radiology. Nov. 1990; 177(2): 385-388.
Sharif H.S., Role of MR imaging in the management of spinal infections. AJR Am J Roentgenol. Jun. 1992;158: 1333-1345.
Star-Lack et al., Improved water and lipid suppression for 3D PRESS CSI using RF bank selective inversion with gradient dephasing (BASING). Magn Reson Med. Aug. 1997;38(2): 311-321.

(56) References Cited

OTHER PUBLICATIONS

Štern et al., Parametric modelling and segmentation of vertebral bodies in 3D CT and MR spine images. Phys Med Biol. Nov. 11, 2011; 56(23): 7505-7522.
Stirling et al., Association between sciatica and Propionibacterium acnes. Lancet. Jun. 23, 2001;357(9273): 2024-2025.
Strickland et al., Development of subject-specific geometric spine model through use of automated active contour segmentation and kinematic constraint-limited registration. J Digit Imaging. Oct. 2011; 24(5): 926-942.
Sutherland et al., Acid-sensing ion channel 3 matches the acid-gated current in cardiac ischemia-sensing neurons. Proc Natl Acad Sci U S A. Jan. 16, 2001;98(2): 711-716.
Swanson et al., Proton HR-MAS Spectroscopy and Quantitative Pathologic Analysis of MRI/3D-MRSI-Targeted Postsurgical Prostate Tissues. Mag Reson Med., Nov. 2003;50(5): 944-954.
Tertti et al., Disc Degeneration in Magnetic Resonance Imaging: A Comparative Biochemical, Histologic, and Radiologic Study in Cadaver Spines. Spine. Jun. 1, 1991;16(6): 629-634.
Thompson et al., Preliminary Evaluation of a Scheme for Grading the Gross Morphology of the Human Intervertebral Disc. Spine. May 1, 1990;15(5): 411-415.
Thompson et al., Modic changes on MR images as studied with provocative diskography: clinical relevance—a retrospective study of 2457 disks. Radiol. Mar. 2009;250(3): 849-855.
Torkki et al., Osteoclast activators are elevated in intervertebral disks with Modic changes among patients operated for herniated nucleus pulposus. Eur Spine J. Jan. 2016;25: 207-216; [Epub Mar. 27, 2015].
Ulrich et al., ISSLS prize winner: repeated disc injury causes persistent inflammation. Spine. Dec. 1, 2007;32(25): 2812-2819.
Urban et al., The Nucleus of the Intervertebral Disc from Development to Degeneration.—Am Zoologist. Feb. 1, 2000;40(1): 53-61.
Urban et al., Nutrition of the intervertebral disc. Spine. Dec. 1, 2004;29(23): 2700-2709.
Urban W., Pathophysiology of the Intervertebral Disc and the Challenges for MRI. J Magn Reson Imaging. Feb. 25, 2007(2):419-32. Feb. 2007;25(2): 4419-432.
Urquhart et al., Could low grade bacterial infection contribute to low back pain? A systematic review. BMC Med. Dec. 2015;13(1): 1-3 in 13 pages.
Valanne et al., CAMP factor homologues in Propionibacterium acnes: A new protein family differentially expressed by types I and II. Microbiology. May 2005;151(5): 1369-1379.
Vos et al., Years lived with disability (YLDs) for 1160 sequelae of 289 diseases and injuries 1990-2010: a systematic analysis for the Global Burden of Disease Study 2010. Lancet. Dec. 15, 2012;380(9859): 2163-2196.
Vowels et al., Induction of proinflammatory cytokines by a soluble factor of Propionibacterium acnes: implications for chronic inflammatory acne. Infect Immun. Aug. 1995;63(8): 3158-3165.
Vrtovec et al., Automated curved planar reformation of 3D spine images. Phys Med Biol. Sep. 14, 2005;50(19): 4527-4540.
Wan et al., PPAR-γ regulates osteoclastogenesis in mice. Nat Med. Dec. 2007;13(12): 1496-1503.
Wang et al., Tumor necrosis factor α- and interleukin-1ß-dependent induction of CCL3 expression by nucleus pulposus cells promotes macrophage migration through CCR1. Arthritis Rheum. Mar. 2013;65(3): 832-842.
Wedderkopp et al., No evidence for presence of bacteria in modic type I changes. Acta Radiol. Jul. 9, 2009;50(1): 65-70.
Weidenbaum et al., Correlating Magnetic Resonance Imaging with the Biochemical Content of the Normal Human Intervertebral Disc. J Ortho Res. Jul. 1992;10(4): 552-561.
Weiler et al., 2002 SSE Award Competition in Basic Science: Expression of major matrix metalloproteinases is associated with intervertebral disc degradation and resorption. Eur Spine J. Aug. 2002;11: 308-320.
Weiner et al., Endplate changes following discectomy: Natural history and associations between imaging and clinical data. Eur Spine J. 2015;24(11):2449-2457; [Published online Dec. 28, 2014].
Wichman H.J., Discography: Over 50 years of controversy. Off Pub State Med Soc Wisconsin. Feb. 1, 2007;106(1): 27-29.
Wolfer et al., Systematic review of lumbar provocation discography in asymptomatic subjects with a meta-analysis of false-positive rates. Pain Physician 2008; 11(4): 513-538.
Wu et al., Quantitative comparison of AIR, SPM, and the fully deformable model for atlas-based segmentation of functional and structural MR images. Hum Brain Mapp. Sep. 2006; 27(9):747-754.
Ziegler et al., LPS-stimulated human bone marrow stroma cells support myeloid cell developmentand progenitor cell maintenance. Ann Hematol. Jan. 2016;95(2): 173-8; [Published online Nov. 11, 2015].
Zuo et al., In-vivo intervertebral disc characterization using magnetic resonance spectroscopy and T1p imaging: association with discography and Oswestry Disability Index and Short Form-36 Health Survey. Spine (Phila PA 1976) Feb. 1, 2012;37(3): 214-221.
Zuo et al., Degradation of chondroitin sulfate proteoglycan enhances the neurite-promoting potential of spinal cord tissue. Exp Neurol. Dec. 1, 1998;154(2): 654-662.
Zuo et al., Chondroitin sulfate proteoglycan with neurite-inhibiting activity is up-regulated following peripheral nerve injury. J Neurobiol. 1998;34(1): 41-54.
Zuo et al., Quantification of relaxation times of metabolite resonance in intervertebral disc using MR Spectroscopy. Proc Inter'l Soc Magn Reson Med. Apr. 18, 2009 (p. 2001).
Zuo et al., MR Spectroscopy in intervertebral disc and correlation with biochemical analysis. Proc Inter'l Soc Magn Reson Med. Apr. 18, 2009 (p. 2002).
Zuo et al., Assessment of Intervertebral Disc Degeneration With Magnetic Resonance Single-Voxel Spectroscopy. Magn Reson Med. Nov. 2009;62(5): 1140-1146; (Sep. 24, 2009).

* cited by examiner

MULTI-VOXEL PRESCRIPTION FOR LUMBAR DISC EVALUATION

BACKGROUND

Field of the Disclosure

This disclosure relates to systems and methods for analysis of medical scans. More specifically, it relates to systems and methods for measuring and evaluating chemical constituents in patient tissue.

Description of the Related Art

Medical scanning systems, such as magnetic resonance imaging (MRI) machines, magnetic resonance spectroscopy (MRS) machines, single photon emission computed tomography/computed tomography (SPECT/CT) machines, and the like generate imagery of internal body tissue. Health care professionals may use the images to identify regions of interest in the tissue.

SUMMARY OF SOME EMBODIMENTS

In some aspects, the techniques described herein relate to a computer-implemented method for performing a magnetic resonance spectroscopy (MRS) scan of a region of interest using a multi-voxel prescription, the computer-implemented method including: under control of a computer system including one or more processors configured to execute specific computer-executable instructions, setting a target chemical shift value for a target voxel associated with the MRS scan of the region of interest; setting an offset chemical shift value for an offset voxel associated with the MRS scan of the region of interest, wherein the offset voxel is spatially offset from the target voxel proportional to a difference between the target chemical shift value and the offset chemical shift value; locating and sizing the target voxel within the region of interest such that the offset voxel, offset from the target voxel, is also within the region of interest; and performing the MRS scan on the region of interest.

In some aspects, the techniques described herein relate to a system including: computer-readable memory storing executable instructions; and one or more processors in communication with the computer-readable memory and programmed by the executable instructions to: set a target chemical shift value for a target voxel associated with a magnetic resonance spectroscopy (MRS) scan of a region of interest; set an offset chemical shift value for an offset voxel associated with the MRS scan of the region of interest, wherein the offset voxel is spatially offset from the target voxel proportional to a difference between the target chemical shift value and the offset chemical shift value; locate and sizing the target voxel within the region of interest such that the offset voxel, offset from the target voxel, is also within the region of interest; and perform the MRS scan on the region of interest.

In some aspects, the techniques described herein relate to a non-transitory computer readable medium storing program instructions for causing a computing device to perform a process including: setting a target chemical shift value for a target voxel associated with a magnetic resonance spectroscopy (MRS) scan of a region of interest; setting an offset chemical shift value for an offset voxel associated with the MRS scan of the region of interest, wherein the offset voxel is spatially offset from the target voxel proportional to a difference between the target chemical shift value and the offset chemical shift value; locating and sizing the target voxel within the region of interest such that the offset voxel, offset from the target voxel, is also within the region of interest; and performing the MRS scan on the region of interest.

BRIEF DESCRIPTION OF THE DRAWINGS

Embodiments of various inventive features will now be described with reference to the following drawings. Throughout the drawings, reference numbers may be re-used to indicate correspondence between referenced elements. The drawings are provided to illustrate example embodiments described herein and are not intended to limit the scope of the disclosure.

DETAILED DESCRIPTION OF SOME EMBODIMENTS

Figure 1:
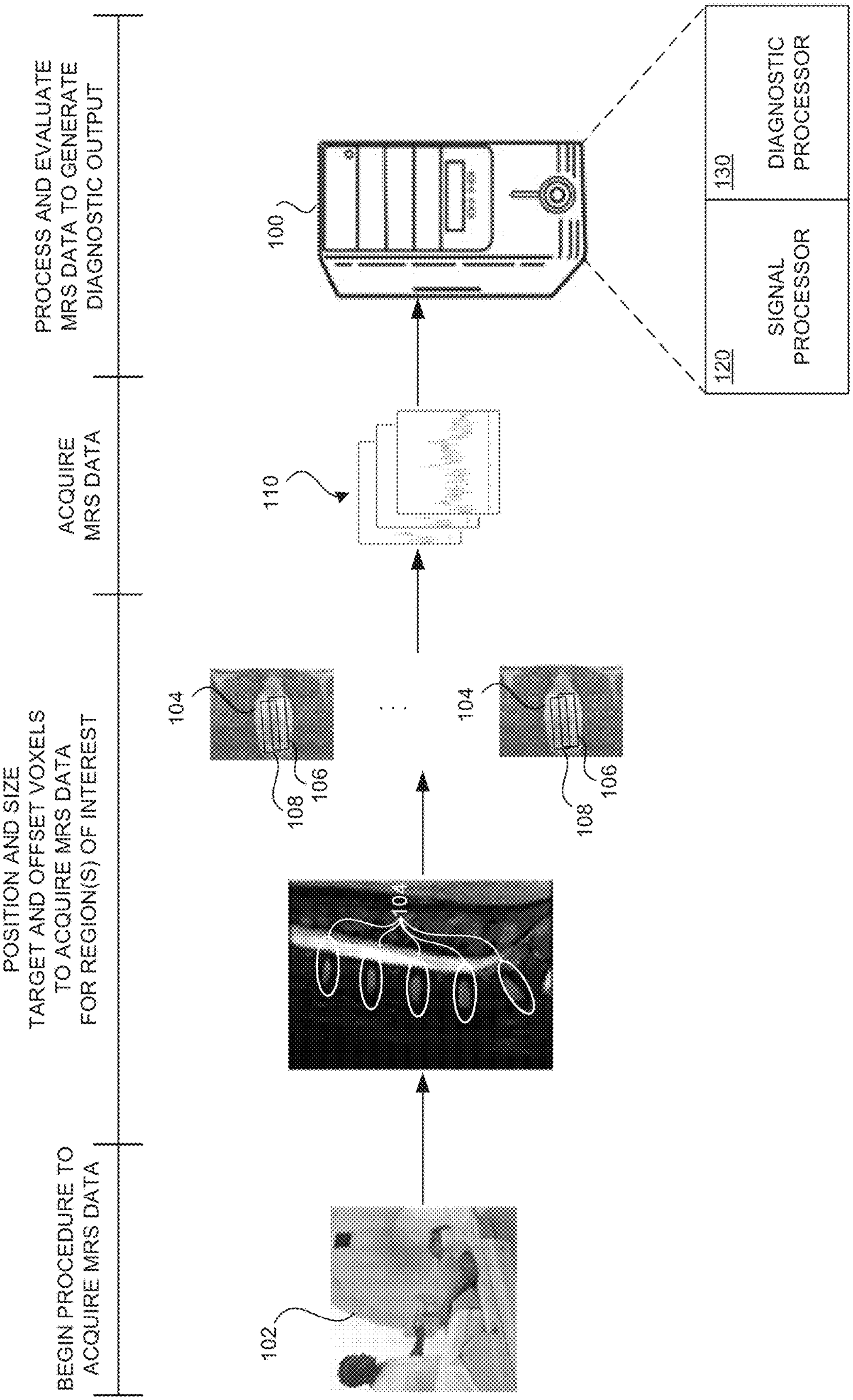
FIG. 1 is a block diagram illustrating an environment for performing magnetic resonance spectroscopy scans using multi-voxel prescription according to some embodiments.

The present disclosure is directed to prescription of multiple voxels for magnetic resonance spectroscopy (MRS) scans. The size and location of the voxels is prescribed such that a desired set of metabolites associated with a desired range of chemical shifts is observed within a confined region of interest, such as a lumbar region of interest.

MRS systems may be used to evaluate the presence and prevalence of metabolites in vivo. In one example, MRS systems may evaluate metabolites present in intervertebral discs to determine the degree to which certain metabolites associated with pain are present. The metabolites may be evaluated based on associated chemical shifts induced and evaluated by MRS systems. Due to the structure and operation of MRS systems, different degrees of physical chemical shift are evaluated at different physical locations with a patient. The different degrees of chemical shift may be defined, compared, or otherwise related to each other in terms of an offset in chemical shift value, while the different corresponding physical locations may be defined, compared, or otherwise related in terms of a spatial offset. For example, the presence of metabolites associated with one particular metric of chemical shift (e.g., as defined in terms of parts per million or "ppm," and sometimes referred to as a target chemical shift value) is detected in one target region, while the presence of metabolites associated with another metric of chemical shift (e.g., a different measurement in ppm, and sometimes referred to as an offset chemical shift value) is detected in a different physical region, spatially offset from the target region. In some cases, the spatial offset from the target region may be several millimeters.

Conventional single-voxel prescription for MRS scans involves placement of a voxel within a region of interest such that a particular target chemical shift is detected at the physical location corresponding to the voxel. For example, placement of the voxel may be performed by manipulating the voxel with respect to an image of a patient's anatomy on a graphical user interface. The voxel is manipulated such that it is located at the region of interest within which evaluation of the target chemical shift is desired. Placement of the voxel may be defined in terms of size and location (e.g., where location is represented by a coordinate location of the center of the voxel or one or more vertices of the voxel, and where size is represented by length, width, and height, or is defined in terms of the coordinates of the voxel vertices). Other chemical shifts, including other chemical shifts of interest, are detected at locations offset from the voxel location, or locations offset from the center of the voxel location. The degree of offset is proportional to the difference in chemical shifts being detected. For example, a voxel may be targeted at a chemical shift of 2.0 ppm (corresponding to proteoglycan), while another chemical shift of interest is 1.3 ppm (corresponding to lipid). The physical location at which chemicals associated with the 1.3 ppm chemical shift are detected is spatially offset from the location of the voxel where chemicals associated with the chemical shift of 2.0 ppm are located. When the entire range of chemical shifts of interest is to be evaluated within a relatively small region of a patient's anatomy, such as a single intervertebral disc, it can be difficult to place the voxel such that the locations of other chemical shifts of interest are also within the region of interest. Ensuring the entire range of chemical shifts of interest are within the patient's anatomical region of interest can be particularly important when structures immediately adjacent to the region of interest include different metabolites, or metabolites that would otherwise interfere with the results of the test. For example, the area immediately adjacent to intervertebral disc regions of interest may be composed of lipids, the detection of which may interfere with MRS test being performed. A time-consuming trial-and-error process may be needed to position the voxel appropriately, involving repeatedly adjusting the placement of the voxel, and evaluating scan results until it is verified that metabolites associated with structures outside the region of interest are not detected. This trial-and-error process may be infeasible, particularly when there are scan limits. For example, procedurally, some scanning centers have a maximum duration per study (e.g., 1 hour per study). Although multiple studies may be done to get around such limits, combining studies is its own complication. As practical matter, patients can only endure and/or pay for a certain amount of scan time (e.g., 1 hour).

Some aspects of the present disclosure relate to prescription of multiple (e.g., two or more) voxels for MRS scans such that a desired range of chemical shifts is observed within a confined region of interest, such as a lumbar region of interest. Advantageously, by visualizing and manipulating the placement of multiple voxels representing an entire range of chemical shifts of interest (or substantially all of the range of interest), the accuracy of MRS scans can be improved or ensured, particularly in small anatomical regions of interest such as intravertebral discs. Moreover, the total time spent performing MRS scans can be reduced, and the trial-and-error method that is sometimes used to avoid scanning outside regions of interest can be avoided.

With reference to an illustrative embodiment, an MRS scan may be performed on one or more intervertebral discs of a patient. An MRS system operator (e.g., a technician or other health care professional) may use a graphical user interface to view an image of the patient's intervertebral discs. The operator may manipulate the placement of a target voxel within a region of interest. Manipulation of the target voxel may automatically cause a corresponding manipulation to a second voxel—also referred to as an offset voxel—that is spatially offset from the target voxel to a degree proportional to a difference between a target chemical shift for the target voxel, and an offset chemical shift for the offset voxel. For example, the target chemical shift may be set to 2.0 ppm, which corresponds to a particular metabolite or set of metabolites that are of particular interest in evaluating a patient for intravertebral disc pain (e.g., proteoglycan). The offset chemical shift may be set to 1.3 ppm, which corresponds to a different metabolite or set of metabolites of particular interest in evaluating the patient for intervertebral disc pain (e.g., lipid). The operator can position the target voxel such that it is as close as possible to the center of the intervertebral disc, and as large as possible to generate a strong signal, while still maintaining the offset voxel within the boundary of the intervertebral disc. In this way, the MRS scan can evaluate the presence and prevalence of the entire range of chemical shifts of interest, while ensuring that such evaluation remains within the physical region of the interest: the patient's intervertebral disc.

Various aspects of the disclosure will now be described with regard to certain examples and embodiments, which are intended to illustrate but not limit the disclosure. Although aspects of some embodiments described in the disclosure will focus, for the purpose of illustration, on particular examples of MRS scans, regions of interest, chemical shift values, and voxel placement methods, the examples are illustrative only and are not intended to be limiting. In some embodiments, the techniques described herein may be applied to additional or alternative types of MRS scans, regions of interest, chemical shift values, voxel placement methods, and the like. In addition, any feature, process, device, or component of any embodiment described and/or illustrated in this specification can be used by itself, or with or instead of any other feature, process, device, or component of any other embodiment described and/or illustrated in this specification.

Example Execution Environment

FIG. 1 shows a general overview of a procedure for generating MRS data regarding one or more regions of interest (ROIs), and evaluating the MRS data using a diagnostic system 100.

In some embodiments, as shown, an MRS system 102 may be used to begin an MRS procedure on a patient. Instead of (or in addition to) image-based output, the MRS system 102 may be configured to produce MRS spectrum data regarding a ROI of the patient. To obtain MRS data for an ROI, multiple voxels 106, 108 may be defined and MRS data 110 may be acquired, as described herein. For example, an MRI image of the region of interest may be generated first, and displayed on an interactive display. Using the interactive display, an operator may define a target voxel 106 to acquire MRS data 110 regarding a target chemical shift for an intervertebral disc 104. An offset voxel 108, for a second chemical shift that is offset from the target chemical shift, may be displayed while the operator is defining the target voxel 106. Accordingly, the operator can visually confirm that that the offset chemical shift will be detected within the ROI. If multiple intervertebral discs 104 are to be evaluated, then multiple sets of voxels 106, 108 may be defined and multiple sets of corresponding MRS data 110 may be acquired (e.g., at least one set of voxels 106, 108 for each intervertebral disc 104).

Although the illustrated example shows the ROIs as a set of intervertebral discs 104 of a patient, the example is provided for illustrative purposes only and is not intended to be limiting, required, or exhaustive. In some embodiments, the diagnostic system 100 may be used to evaluate MRS data regarding other ROIs.

The acquired MRS scan data (also referred to herein as "MRS acquisition data" or "MRS scan data", or simply as "acquisition data" or "scan data" for brevity) may be processed by the diagnostic system 100. The diagnostic system 100 may include various subsystems for processing acquisition data and generating diagnostic output. For example, the diagnostic system 100 may include a signal processor 120 to process the acquisition data and generate processed MRS data (also referred to as "spectrum data"). The diagnostic system 100 may also include a diagnostic processor 130 that evaluates the spectrum data. In some embodiments, the diagnostic processor 130 may use one or more machine learning (ML) models to generate model output data representing diagnostic classifications (e.g., positive or negative for pain in an ROI), acquisition quality classifications (e.g., positive or negative for indicators of low-quality acquisition data), or both. The diagnostic system 100 may use the model output data to generate diagnostic output.

Figure 5:
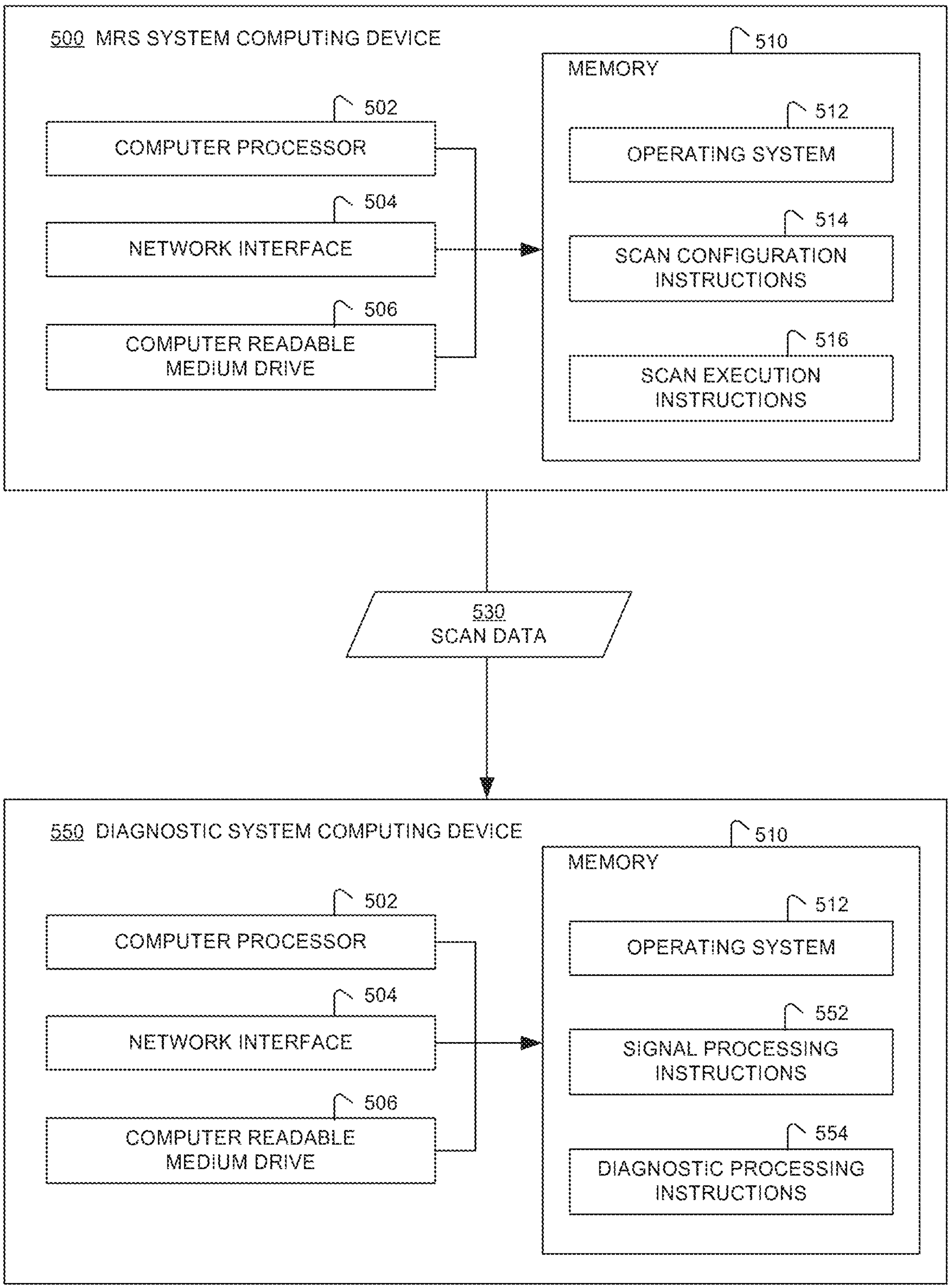
FIG. 5 illustrates various components of an example MRS system computing device and MRS scan diagnostic computing device configured to implement aspects of the present disclosure according to some embodiments.

The diagnostic system 100 may be a logical association of one or more computing systems for processing acquisition data and generating diagnostic output using ML models. The diagnostic system 100 (or individual components or subsystems thereof) may be implemented on one or more physical computing systems such as blade servers, midrange computing devices, mainframe computers, desktop computers, or any other computing device configured to provide computing services and resources. One example of a diagnostic system computing device 550 on which the diagnostic system 100 may be implemented is shown in FIG. 5. The diagnostic system 100 may include any number of such computing devices.

In some embodiments, the features and services provided by the diagnostic system 100 may be implemented as web services consumable via one or more communication networks. In further embodiments, the diagnostic system 100 (or individual components thereof) are provided by one or more virtual machines implemented in a hosted computing environment. The hosted computing environment may include one or more rapidly provisioned and released computing resources, such as computing devices, networking devices, and/or storage devices. A hosted computing environment may also be referred to as a "cloud" computing environment.

In some embodiments, the signal processor 120 may include various sub-components and processors that carry out certain steps, such as a channel selector that conducts channel or "coil" selection, a phase corrector that does phase correction, an apodizer that conducts apodization, a domain transformer that conducts domain transformation (e.g., transformation of data from time domain to frequency domain), a frame editor that conducts frame editing, a frequency corrector that conducts frequency correction, and a channel combiner that conducts combining or averaging steps to aggregate retained channels into one final post-processed spectral results, other components, or some combination thereof. The post-processed spectral results may be referred to as spectrum data.

Following the signal processing steps, the diagnostic processor 130 may conduct diagnostic processing of the spectrum data using one or more components, such as a data extractor, a disc assessment subsystem, a diagnostic report generator, other components, or some combination thereof. The data extractor may process spectrum data into a form that that may be input into the disc assessment subsystem, which may evaluate the input data and assess one or more ROIs. The diagnostic report generator may produce an output presentation based on output of the ML model-based disc assessment subsystem.

The components discussed above are illustrative only, and are not intended to be limiting, required, or exhaustive. In some embodiments, additional, fewer, and/or alternative components may be used. Some embodiments of the components discussed above, and examples of the operations performed by the components, are described in U.S. Patent Application Publication No. 2019/0307393 and U.S. Patent Application Publication No. 2023/0140742, the content of each of which is incorporated by reference herein and forms part of this specification. U.S. Pat. Nos. 10,285,622; 9,280,718; 10,045,711; and 9,901,285 are hereby incorporated by reference herein and form part of this specification. The systems and methods disclosed herein can use various features disclosed in these references.

With reference to an illustrative example, as described in U.S. Patent Application Publication No. 2019/0307393, the signal processor 120 is configured to generate a diagnostically useful MRS spectrum from a region of interest, such as an intervertebral disc of a patient. The MRS spectrum data may be used for measuring spectral information corresponding to various chemicals (e.g., propionic acid (PA), lactic acid (LA), alanine (AL), and structural chemicals of proteoglycan (PG) and collagen or carbohydrate (CA)) to diagnose and/or monitor various conditions. Certain applications include diagnosing painful and non-painful discs in chronic, severe low back pain patients (DDD-MRS). The signal processor 120 generates or otherwise acquires DDD-MRS spectra within intervertebral disc nuclei to produce a processed spectrum, with spectral regions corresponding to certain chemicals. A diagnostic processor 130 may then determine a diagnostic classification for each disc using one or more ML models. Diagnostic information may then be presented and used in a manner that is helpful for distinguishing degenerative painful vs. non-painful discs. For example, a diagnostic display may provide a scaled, color coded legend and indication of results for each disc analyzed, which is shown with and/or as an overlay onto an MRI image of the lumbar spine region for the patient being evaluated. Clinical application of the embodiments provides a non-invasive, objective, pain-free, reliable approach for diagnosing painful vs. non-painful discs by simply extending and enhancing the utility of otherwise standard MRI exams of the lumbar spine, and/or monitoring such chemicals.

MRS Scanning with Multi-Voxel Prescription

Figure 2:
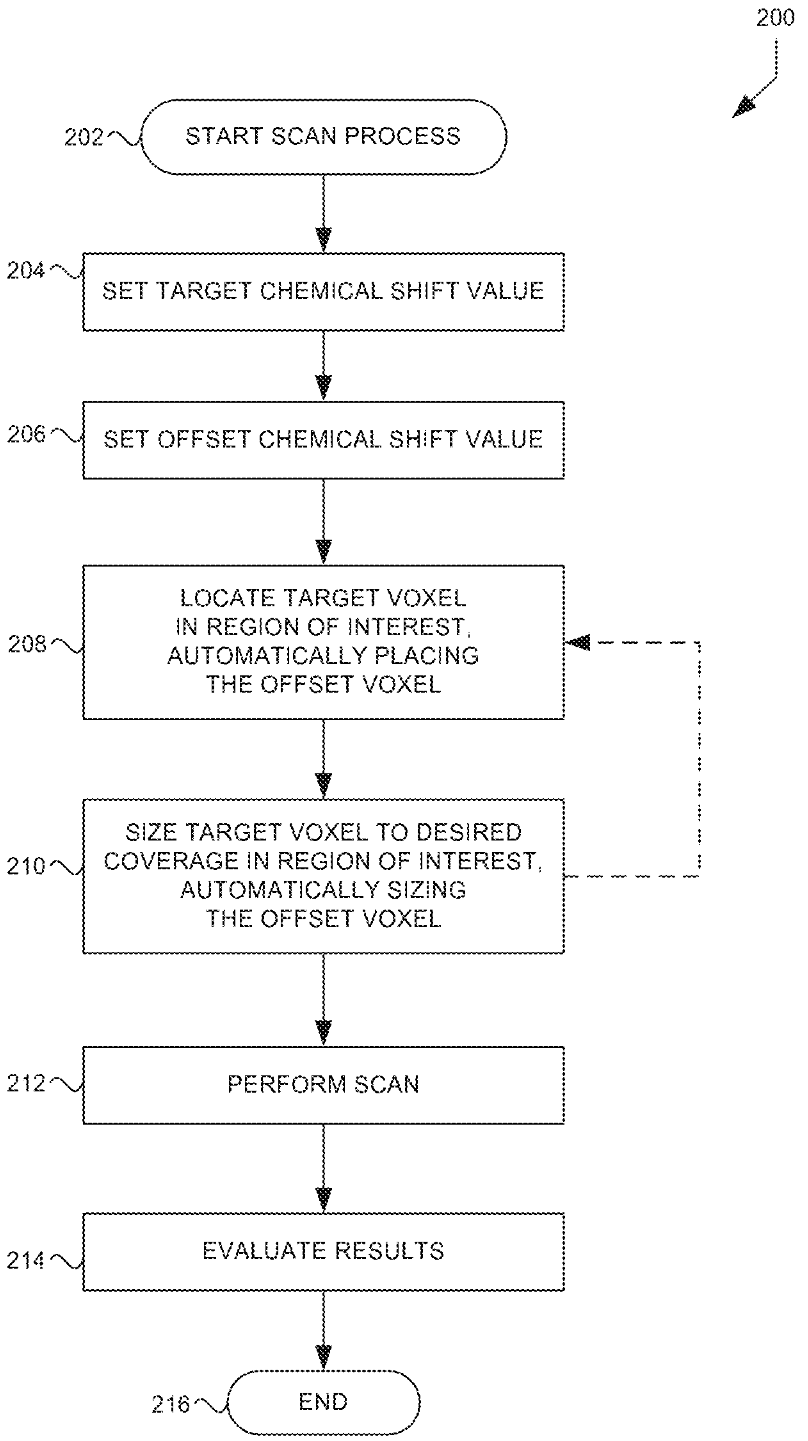
FIG. 2 is a flow diagram of an illustrative routine for performing magnetic resonance spectroscopy scans using multi-voxel prescription according to some embodiments.

With reference to an illustrative embodiment, FIG. 2 shows an example routine 200 for configuring and executing an MRS scan using a multi-voxel prescription. Portions of the routine 200 will be described with further reference to the illustrative user interface shown in FIG. 3, and the illustrative scan results shown in FIG. 4.

The routine 200 begins at block 202. The routine 200 may be a computer-implemented method that begins in response to an event, such as when an MRS system 102 operator accesses a scan configuration interface. When the routine 200 is initiated, a set of executable program instructions stored on one or more non-transitory computer-readable media (e.g., hard drive, flash memory, removable media, etc.) may be loaded into memory (e.g., random access memory or "RAM") of a computing device, such as the MRS system computing device 500 shown in FIG. 5 and described in greater detail below. In some embodiments, the routine 200 or portions thereof may be implemented on multiple processors, serially or in parallel.

At block 204, the MRS system 102 may set a target chemical shift value for the MRS scan. The target chemical shift value may correspond to a particular metabolite of interest or group of metabolites of interest, or the target chemical shift value may correspond to a location within a range of metabolites of interest. For example, the target chemical shift may be set such that it is at the center of a range of metabolites of interest. As another example, the target chemical shift value is set to a chemical shift that is of particular interest and is closest to the midpoint of the chemical shift range of the interest in comparison with all other chemical shifts that may be of particular interest. As a further example, the target chemical shift may be set to one end, or near one end, of the chemical shift range of interest.

In one specific non-limiting embodiment, the chemical shift range of interest is from 0.0 ppm to 4.0 ppm, or about 0.0 ppm to about 4.0 ppm (e.g., 0.0 ppm to 4.0 ppm, where the value for one or both endpoints is +/−0.01 ppm, +/−0.05 ppm, +/−0.1 ppm, or +/−0.5 ppm). In this case, the target chemical shift value may be set to the center of the chemical shift range of interest, such as a value within a range of about 2.05 ppm to about 1.95 ppm. For example, the target chemical shift value may be set to 2.0 ppm. The MRS system 102 may produce the strongest or best signal (e.g., in terms of signal to noise ratio) at the target chemical shift value. Therefore, setting the target chemical shift value to the center of the range can ensure that the best signal is also centered in the chemical shift range of interest.

In another embodiment, the target chemical shift value may be set a chemical shift at or near an end of the range of interest. If the chemical shift range of interest is 0.0 ppm to 4.0 ppm, then the target chemical shift may be set to about 0.0 ppm or 4.0 ppm. Setting the target chemical shift value at or near an end of the chemical shift range of interest can help the operator to visually ensure the physical area scanned for the entire chemical shift range of interest is within a region of interest (e.g., an intervertebral disc), as discussed in greater detail below.

At block 206, the MRS system 102 may set an offset chemical shift value for the MRS scan. The offset chemical shift value may correspond to a particular chemical of interest or group of chemicals of interest, or the chemical shift value may correspond to a location within a range of chemical shifts of interest (e.g., one end of the range).

Returning to the example above, in which the range of chemical shifts of interest is from 0.0 ppm to 4.0 ppm (or about 0.0 ppm to about 4.0 ppm), the offset chemical shift value may be set at, near, or outside one end of the chemical shift range of interest. In this case, the offset chemical shift value may be within a range of about 0.95 ppm to about 1.05 ppm, or within a range of about 1.25 ppm to about 1.35 ppm. For example, the offset chemical shift value may be set to 1.3 ppm, which corresponds to lipids that may be detected by the MRS scan. Lipids may be chosen to so that when the target voxel is positioned as described in greater detail below, the operator can ensure that the secondary voxel corresponding to the offset chemical shift (lipids) is not at the intervertebral endplate, which is primarily lipids and would affect results of the MRS scan. As another example, the offset chemical shift value may be set to 1.0 ppm.

Figure 3:
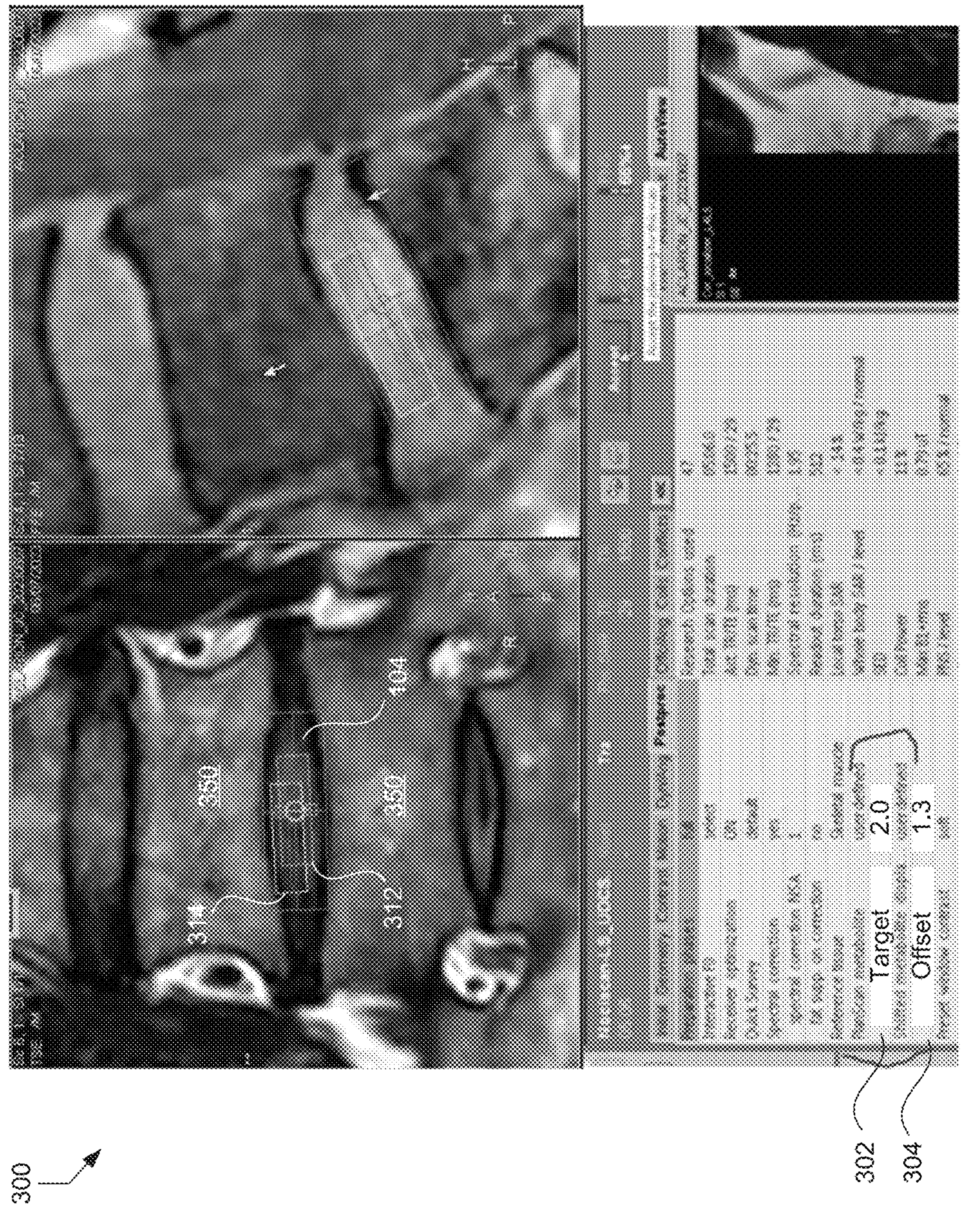
FIG. 3 is a diagram of an illustrative MRS system interface for configuring an MRS scan with multi-voxel prescription according to some embodiments.

FIG. 3 illustrates an example interface 300 in which an operator may configure aspects of an MRS scan, including specification of chemical shifts and placement of voxels. As shown, an operator may specify, in target chemical shift field 302, the target chemical shift for the scan. The operator may also specify, in offset chemical shift field 304, the offset chemical shift for the scan. In some embodiments, the fields may be pre-filled with default values, such as the 2.0 and 1.3 values of the examples above. In some embodiments, rather than being pre-filled with default values, the operator may enter the values based on instructions for performing the MRS scan.

Figure 4:
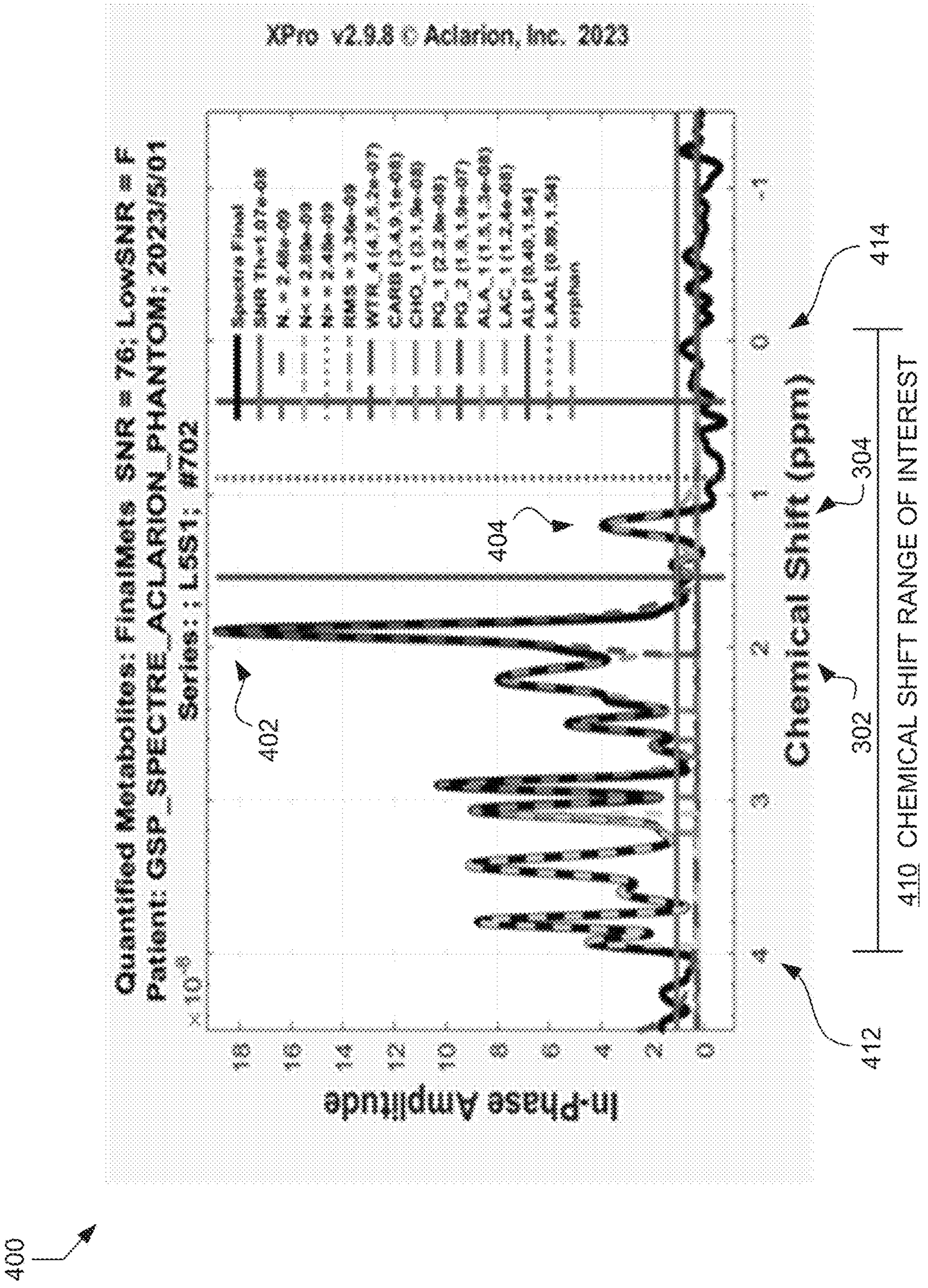
FIG. 4 is a diagram of an illustrative spectral plot resulting from an MRS scan according to some embodiments.

FIG. 4 is a diagram of example MRS results 400, showing a spectral plot covering a range of chemical shifts that are detected as a result of an MRS scan. As shown, the MRS results 400 range from less than −1.0 ppm to greater than 4.0 ppm. However, the chemical shift range of interest 410 reflects the example discussed above: from a minimum value 414 of 0.0 ppm to a maximum value 412 of 4.0 ppm.

Returning to FIG. 2, at block 208, the MRS system 102 may locate the target voxel within the region of interest. The operator may position the target voxel within a region of interest using a graphical user interface. For example, the operator may place or drag the voxel to a region of interest using a touch screen or peripheral pointing device. As another example, the operator may enter coordinates, and location may be visually represented on the interface for confirmation by the operator.

As shown in FIG. 3, the target voxel 312 may be positioned within a patient's intervertebral disc 104, using an image of the patient's lumbar region. In the example MRI image shown, the intervertebral disc 104 appears as a dark region between two lighter regions, which correspond to two of the patient's vertebrae 350. The target voxel 312 appears as a rectangle that may be moved (e.g., dragged or placed interactively, or by entering different coordinates) within the intervertebral disc 104.

In the example shown, the operator has positioned the target voxel 312 in substantially the center of the intervertebral disc 104. In some implementations, the target voxel location is where the strongest MRS signal is obtained (e.g., in terms of signal-to-noise ratio) compared to locations outside of the target voxel, including the offset voxel described below. Thus, positioning the target voxel 312 in the center of the region of interest (the patient's intervertebral disc 104 in this example) provides the strongest signal at a location that is farthest from surrounding tissue that may interfere with desired MRS scan results, such as the vertebral endplates and the vertebra themselves. As discussed above with respect to block 204, when a range of chemical shifts is of interest, the target chemical shift value for the target voxel 312 is advantageously set to the midpoint (or substantially the midpoint) of the chemical shift range of interest.

The chemical shift value for the target voxel 312 and the placement of the target voxel 312 within the region of interest affect each other, and therefore they are jointly determined to produce a desired result. For example, if the target voxel 312 were to be placed away from the center of the region of interest (e.g., closer to a boundary of the region of interest), then the target chemical shift of the target voxel 312 is likewise set to a value that is away from the middle of the chemical shift range of interest (e.g., closer to an endpoint of the chemical shift range of interest), and vice versa.

In some embodiments, the position of the offset voxel 314 is automatically determined from the configuration of the target voxel 312 (the target voxel position and target chemical shift value), in combination with the offset chemical shift value. In the example shown, the offset voxel 314 is positioned near the edge of the region of interest: the patient's intervertebral disc 104. In particular, the offset voxel 314 is positioned near the vertebral endplate of a vertebra 350. The degree to which the offset voxel 314 is offset from the target voxel 312 may be directly proportionate to the degree to which the target chemical shift value differs from the offset chemical shift value. If the offset chemical shift value is only incrementally greater or less than the target chemical shift value (e.g., a target chemical shift value of 2.0, and an offset chemical shift value of 1.9), then the voxels may overlap substantially. In contrast, if the offset chemical shift value differs more substantially from the target chemical shift value, then the degree of overlap may be reduced accordingly. For example, when the target chemical shift value is 2.0 and the offset chemical shift value is 1.3 as shown, the target voxel 312 and offset voxel 314 may overlap about 50% of their total area. In an extreme case, where the target chemical shift value and offset chemical shift value differ significantly, there may be little to no overlap of the target voxel 312 and offset voxel 314.

The interface 300 may automatically adjust the position of the offset voxel 314 in response to various interaction events. For example, when the operator moves the target voxel 312, the offset voxel 314 may automatically move in tandem, retaining the degree of offset proportional to the difference between the target chemical shift value and the offset chemical shift value. Thus, the operator may manipulate the position of the of the target voxel 312 such that the offset voxel 314 is also within the region of interest or is otherwise positioned at a desirable location. As another example, when the operator changes either the offset chemical shift value or the target chemical shift value, the location of the offset voxel 314 may automatically adjust such that the offset from the target voxel 312 visually corresponds to the difference between the target chemical shift value and the offset chemical shift value. Thus, the operator may manipulate the target chemical shift or the offset chemical shift such that the offset voxel 314 is also within the region of interest or is otherwise positioned at a desirable location.

At block 210, the MRS system 102 may size the target voxel 312 within the region of interest. The size of the target voxel 312 can affect the quality of the signal obtained during the MRS scan. If the target voxel 312 is too small, the signal may be low in quality (e.g., a low signal-to-noise ratio). If the target voxel 312 is too large, it may encompass areas outside the region of interest.

The operator may interact with an interface to size the target voxel 312, such as by dragging a corner or edge of the voxel to resize it, by entering size measurements (e.g., length and width), by entering coordinates for corners, etc. Beneficially, sizing the target voxel 312 may automatically adjust the size of the offset voxel 314. For example, when the operator drags a corner or edge of the target voxel 314 or endites size measurements, the offset voxel 314 may resize in tandem. Thus, the operator may manipulate the size of the of the target voxel 312 such that the offset voxel 314 is within the region of interest or is otherwise positioned at a desirable location.

The location and sizing operations described with respect to blocks 208 and 210 may be performed iteratively, until a desired size and location of both the target voxel 312 and offset voxel 314 are achieved. In some embodiments, the operations may be performed in a different order, or individual operations may be repeated before—or without—performing the other operation.

At block 212, the MRS system may perform an MRS scan, and a block 214 the results of the scan may be evaluated. In the example shown in FIG. 4, the target chemical shift value 302, set at 2.0, corresponds to a peak 402 in a detected chemical shift of interest. The offset chemical shift value 304, set at 1.3, corresponds to a peak 404 in another detected chemical shift of interest.

Examples of performing MRS scans and evaluating results are disclosed in U.S. Patent Application Publication No. 2019/0307393, U.S. Patent Application Publication No. 2023/0140742, U.S. Pat. Nos. 10,285,622, 9,280,718, 10,045,711, and 9,901,285, incorporated by reference above.

At block 216, routine 200 may terminate.

Aspects of the multi-voxel prescription described herein may be combined with aspects of the disclosures incorporated by reference. With reference to one illustrative combination, U.S. Pat. No. 9,280,718 discloses generation of an "AutoVox" data structure that contains information to create a 3D volume, such as a rectilinear cube, within which a voxel is automatically defined for scanning. The multi-voxel prescription described herein may be used to generate the boundaries of such a 3D volume. For example, two voxels may be used to define outer boundaries within a region of interest (e.g., within an intravertebral disc) such that the physical chemical shifts of interest also remain within the region of interest (e.g., not encompassing any part of the vertebral endplates on either side of the disc). Within the 3D volume bounded by the multiple voxels, a target voxel can be determined using the disclosed automated methods.

Example Computing Devices

FIG. 5 illustrates an example MRS system computing device 500 that may be used in some embodiments to execute the processes and implement the features of the MRS system 102 described above. In some embodiments, the MRS system computing device 500 may include: one or more computer processors 502, such as physical central processing units (CPUs) or graphics processing units (GPUs); one or more network interfaces 504, such as a network interface cards (NICs); one or more computer readable medium drives 506, such as high density disks (HDDs), solid state drives (SSDs), flash drives, and/or other persistent non-transitory computer-readable media; and one or more computer-readable memories 510, such as random access memory (RAM) and/or other volatile non-transitory computer-readable media. The network interface 504 can provide connectivity to one or more networks or computing devices. The computer processor 502 can receive information and instructions from other computing devices or services via the network interface 504. The network interface 504 can also store data directly to the computer-readable memory 510. The computer processor 502 can communicate to and from the computer-readable memory 510, execute instructions and process data in the computer-readable memory 510, etc.

The computer-readable memory 510 may include computer program instructions that the computer processor 502 executes in order to implement one or more embodiments. The computer-readable memory 510 can store an operating system 512 that provides computer program instructions for use by the computer processor 502 in the general administration and operation of the training system computing device 500. The computer-readable memory 510 can also include scan configuration instructions 514 for configuring an MRS scan using multi-voxel prescription. The computer-readable memory 510 can also include scan execution instructions 516 for performing an MRS scan. The computer-readable memory 510 can further include other computer program instructions and data for implementing aspects of the present disclosure.

FIG. 5 also illustrates various components of an example diagnostic system computing device 550 configured to implement various functionality of the diagnostic system 100.

In some embodiments, as shown, the diagnostic system computing device 550 may include: one or more computer processors 502, such as physical central processing units (CPUs); one or more network interfaces 504, such as a network interface cards (NICs); one or more computer readable medium drives 506, such as a high density disk (HDDs), solid state drives (SSDs), flash drives, and/or other persistent non-transitory computer-readable media; and one or more computer-readable memories 510, such as random access memory (RAM) and/or other volatile non-transitory computer-readable media.

The computer-readable memory 510 may include specific instructions (e.g., computer program instructions) that one or more computer processors 502 execute in order to implement one or more embodiments. The computer-readable memory 510 can store an operating system 512 that provides computer program instructions for use by the computer processor(s) 502 in the general administration and operation of the diagnostic system computing device 550.

In some embodiments, the computer-readable memory 510 can further include computer program instructions and other information for implementing aspects of the present disclosure, such as processing scan data 530 received from the MRS system computing device 500. For example, the computer-readable memory 510 may include signal processing instructions 552 for managing the signal processing operations of the signal processor 120. As another example, the computer-readable memory 510 may include diagnostic processing instructions 554 for performing the functions of the diagnostic processor 130.

Terminology

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware, or combinations of electronic hardware and computer software. To clearly illustrate this interchangeability, various illustrative components, blocks, modules, and steps have been described above generally in terms of their functionality. Whether such functionality is implemented as hardware, or as software that runs on hardware, depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

The following is claimed:

1. A computer-implemented method for performing a magnetic resonance spectroscopy (MRS) scan of a region of interest using a multi-voxel prescription, the computer-implemented method comprising:

under control of a computer system comprising one or more processors configured to execute specific computer-executable instructions, setting a target chemical shift value for a target voxel associated with the MRS scan of the region of interest;

setting an offset chemical shift value for an offset voxel associated with the MRS scan of the region of interest, wherein the offset voxel is spatially offset from the target voxel proportional to a difference between the target chemical shift value and the offset chemical shift value;

locating and sizing the target voxel within the region of interest such that the offset voxel, offset from the target voxel, is also within the region of interest; and performing the MRS scan on the region of interest based on the target voxel and the offset voxel.

2. A system comprising:

computer-readable memory storing executable instructions; and one or more processors in communication with the computer-readable memory and programmed by the executable instructions to:

set a target chemical shift value for a target voxel associated with a magnetic resonance spectroscopy (MRS) scan of a region of interest;

set an offset chemical shift value for an offset voxel associated with the MRS scan of the region of interest, wherein the offset voxel is spatially offset from the target voxel proportional to a difference between the target chemical shift value and the offset chemical shift value;

locate and sizing the target voxel within the region of interest such that the offset voxel, offset from the target voxel, is also within the region of interest; and perform the MRS scan on the region of interest based on the target voxel and the offset voxel.

3. A non-transitory computer readable medium storing program instructions for causing a computing device to perform a process comprising:

setting a target chemical shift value for a target voxel associated with a magnetic resonance spectroscopy (MRS) scan of a region of interest;

setting an offset chemical shift value for an offset voxel associated with the MRS scan of the region of interest, wherein the offset voxel is spatially offset from the target voxel proportional to a difference between the target chemical shift value and the offset chemical shift value;

locating and sizing the target voxel within the region of interest such that the offset voxel, offset from the target voxel, is also within the region of interest; and performing the MRS scan on the region of interest.

4. The computer-implemented method of claim 1, wherein setting the target chemical shift value for the target voxel comprises setting the target chemical shift value to about 2 parts per million.

5. The computer-implemented method of claim 1, wherein setting the offset chemical shift value for offset voxel comprises setting the offset chemical shift value to about 1.3 parts per million.

6. The computer-implemented method of claim 1, wherein locating and sizing the target voxel within the region of interest comprises locating the target voxel in a substantially central location within the region of interest.

7. The computer-implemented method of claim 1, wherein the offset voxel is automatically repositioned within the region of interest based on repositioning the target voxel.

8. The computer-implemented method of claim 1, wherein the offset voxel is automatically repositioned within the region of interest based on a change to at least one of the target chemical shift value or the offset chemical shift value.

9. The computer-implemented method of claim 1, wherein performing the MRS scan on the region of interest comprises performing the MRS scan on a lumbar region of interest.

10. The computer-implemented method of claim 1, further comprising diagnosing a source of pain based on a result of the MRS scan.

11. The system of claim 2, wherein to set the target chemical shift value for the target voxel, the one or more processors are further programmed by the executable instructions to set the target chemical shift value to about 2 parts per million.

12. The system of claim 2, wherein to set the offset chemical shift value for offset voxel, the one or more processors are further programmed by the executable instructions to set the offset chemical shift value to about 1.3 parts per million.

13. The system of claim 2, wherein to locate and size the target voxel within the region of interest, the one or more processors are further programmed by the executable instructions to limit a size of the target voxel such that the offset voxel remains entirely within the region of interest.

14. The system of claim 2, wherein the offset voxel is automatically repositioned within the region of interested based on repositioning the target voxel.

15. The system of claim 2, wherein the offset voxel is automatically repositioned within the region of interest based on a change to one of the target chemical shift value or the offset chemical shift value.

16. The non-transitory computer readable medium of claim 3, wherein setting the target chemical shift value for the target voxel comprises setting the target chemical shift value to about 2 parts per million.

17. The non-transitory computer readable medium of claim 3, wherein setting the offset chemical shift value for offset voxel comprises setting the offset chemical shift value to about 1.3 parts per million.

18. The non-transitory computer readable medium of claim 3, wherein locating and sizing the target voxel within the region of interest comprises locating the target voxel in a substantially central location within the region of interest.

19. The non-transitory computer readable medium of claim 3, wherein the offset voxel is automatically repositioned within the region of interest based on repositioning the target voxel.

20. The computer-implemented method of claim 9, wherein performing the MRS scan on the lumbar region of interest comprises performing the MRS scan on an intervertebral disc.

* * * * *